US012644150B2

(12) United States Patent
Hoffmann et al.

(10) Patent No.: US 12,644,150 B2
(45) Date of Patent: Jun. 2, 2026

(54) MEMBRANE-BASED, IN-GEL LOOP-MEDIATED ISOTHERMAL AMPLIFICATION (LAMP) SYSTEM AND METHOD FOR DETECTING MICROBES

(71) Applicant: California Institute of Technology, Pasadena, CA (US)

(72) Inventors: Michael R. Hoffmann, South Pasadena, CA (US); Jing Li, Pasadena, CA (US); Yanzhe Zhu, Pasadena, CA (US); Xunyi Wu, Pasadena, CA (US); Alan Yalun Gu, Pasadena, CA (US); Leopold Dobelle, Pasadena, CA (US); Clement A. Cid, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 406 days.

(21) Appl. No.: 17/508,751

(22) Filed: Oct. 22, 2021

(65) Prior Publication Data

US 2022/0162686 A1 May 26, 2022

Related U.S. Application Data

(60) Provisional application No. 63/117,932, filed on Nov. 24, 2020.

(51) Int. Cl.
*C12Q 1/6853* (2018.01)
*C12Q 1/6832* (2018.01)

(52) U.S. Cl.
CPC ......... *C12Q 1/6853* (2013.01); *C12Q 1/6832* (2013.01)

(58) Field of Classification Search
CPC .................................................. C12Q 1/6844
See application file for complete search history.

(56) References Cited

U.S. PATENT DOCUMENTS

2004/0079763 A1* 4/2004 Powell ............... B65D 81/3266
222/107
2016/0362718 A1 12/2016 Mach et al.
2017/0275696 A1 9/2017 Xu et al.

FOREIGN PATENT DOCUMENTS

WO 2020/047077 A1 3/2020

OTHER PUBLICATIONS

Cai et al. "Optical absorption in transparent PDMS materials applied for multimode waveguides fabrication." Optical materials 30.7 (2008): 1157-1161 (Year: 2008).*

(Continued)

*Primary Examiner* — Aaron A Priest
*Assistant Examiner* — Tian Yu
(74) *Attorney, Agent, or Firm* — Gavrilovich, Dodd & Lindsey LLP

(57) ABSTRACT

Disclosed herein is a membrane-based, in-gel loop-mediated isothermal amplification (LAMP) system, kit and method for detection of a target microorganism in a sample suspected of containing the microorganism. LAMP reagents, a lysing agent and a hydrogel are placed together on a filter membrane loaded with a pre-filtered sample. The hydrogel polymerizes over a short time to immobilize any target DNA/RNA particles on the membrane. The system may include a compact, portable device that integrates heat incubation and fluorescence illumination, and also a cloud-based smartphone image analysis application for quantitative results interpretation. If target DNA/RNA are present in the sample, fluorescent amplicons are produced as a result of LAMP reaction. The target microorganisms are detected by visually detecting the presence or absence of the amplicons. The method may be employed for rapid and inexpensive point-of-use (POU) absolute quantification of SARS-CoV-2

(Continued)

in environmental water or wastewater samples with high sensitivity.

17 Claims, 11 Drawing Sheets

Specification includes a Sequence Listing.

(56)                References Cited

OTHER PUBLICATIONS

Shehadul et al., A Review on Macroscale and Microscale Cell Lysis Methods. Micromachines (Basel). Mar. 8, 2017;8(3):83. doi: 10.3390/mi8030083. PMCID: PMC6190294 (Year: 2017).*

Lin et al. Digital Loop-Mediated Isothermal Amplification on a Commercial Membrane. ACS Sens. Jan. 25, 2019;4(1):242-249. doi: 10.1021/acssensors.8b01419. Epub Jan. 15, 2019. PMID: 30604619; PMCID: PMC6350201 (Year: 2019).*

Louten J. Virus Structure and Classification. Essential Human Virology. 2016:19-29. doi: 10.1016/B978-0-12-800947-5.00002-8. Epub May 6, 2016. PMCID: PMC7150055 (Year: 2016).*

Kashir J, Yaqinuddin A. Loop mediated isothermal amplification (LAMP) assays as a rapid diagnostic for COVID-19. Med Hypotheses. Aug. 2020; 141:109786. doi: 10.1016/j.mehy.2020.109786. Epub Apr. 25, 2020. PMID: 32361529; PMCID: PMC7182526. (Year: 2020).*

Lin et al. Asymmetric Membrane for Digital Detection of Single Bacteria in Milliliters of Complex Water Samples. ACS Nano. Oct. 23, 2018;12(10):10281-10290. doi10.1021/acsnano.8b05384. Epub Sep. 19, 2018. PMID: 30211534; PMCID: PMC6202633 (Year: 2018).*

Huang et al., Smartphone-Based in-Gel Loop-Mediated Isothermal Amplification (gLAMP) System Enables Rapid Coliphage MS2 Quantification in Environmental Waters. Environ Sci Technol. Jun. 5, 2018;52(11):6399-6407. doi: 10.1021/acs.est.8b00241. Epub May 16, 2018. PMID: 29738236; PMCID: PMC5990930 (Year: 2018).*

Duplex Drug-Delivery Pouch; packagingdigest.com; Published Nov. 18, 2014 (Year: 2014).*

Rodriquez, Kari, International Search Report and Written Opinion, PCT/US2021/056309, International Searching Authority, United States Patent and Trademark Office, Jan. 28, 2022.

Wang, Xin, International Preliminary Report on Patentability and Written Opinion, PCT/US2021/056309, International Bureau of WIPO, Jun. 8, 2023.

* cited by examiner

40

MEMBRANE-BASED, IN-GEL LOOP-MEDIATED ISOTHERMAL AMPLIFICATION (LAMP) SYSTEM AND METHOD FOR DETECTING MICROBES

CROSS REFERENCE TO RELATED APPLICATIONS

This application claims the benefit of U.S. Provisional Patent Application Ser. No. 63/117,932, filed on Nov. 24, 2020, which is incorporated by reference herein in its entirety.

TECHNICAL FIELD

The present disclosure generally relates to techniques for detecting microbes of interest in a sample, and more particularly, to detection techniques based on loop-mediated isothermal amplification (LAMP).

INCORPORATION BY REFERENCE OF SEQUENCE LISTING

Accompanying this filing is a Sequence Listing entitled "Sequence-Listing ST25.txt", created on Oct. 22, 2021, and having 16,616 bytes of data, machine formatted on IBM-PC, MS-Windows operating system. The sequence listing is hereby incorporated herein by reference in its entirety for all purposes.

BACKGROUND

The detection and quantification of microbial pathogens (e.g., viruses, bacteria and protozoa) in environmental and wastewaters can be challenging due to their low concentrations, impurities and inhibitors present in the water, and the complexity of known detection methods and instruments.

The Covid-19 pandemic has underscored the need for detecting pathogenic microorganisms in environmental and wastewaters. Detection of SARS-CoV-2 RNA in river water and wastewater has been widely reported globally such as in Italy, Japan, and Brazil. SARS-CoV-2 RNA may persist in environmental waters. Thus, large-scale environmental surveillance is desirable for quantitative risk assessment, for notice of potential outbreaks, population-wide infection prevalence monitoring, and for a better understanding of contamination and potential spread via environmental waters.

However, known microorganism testing and detection technologies have considerable limitations for large-scale environmental surveillance in that they generally use specialized equipment, highly-trained personnel, and labor-intensive laboratory procedures.

For example, a known method of detecting pathogens is based on nucleic acid analysis (NAA) using primarily reverse transcription quantitative polymerase chain reaction (RT-qPCR). However, RT-qPCR is not readily adaptable for large-scale environmental surveillance, especially in resource-limited settings, due to its requirement for a specialized thermocycling instrumentation and the need for highly-trained personnel. Furthermore, RT-qPCR does not typically produce absolute quantification. In addition, RT-qPCR targeting certain pathogens may be sensitive to inhibitors that are present in environmental water or wastewater leading to false negative results.

To address these challenges, other types of detection methods, for example, isothermal NAA methods, such as loop-mediated isothermal amplification (LAMP), have been used for environmental quantification of certain microbial pathogens, for example, the Zika virus, astrovirus, MS2, *E. coli*, and *Enterococcus* spp. For example, US Published Patent Application 2019/0203268 A1 discloses a portable in-gel LAMP platform for the sensitive detection of MS2 coliphage in wastewater, where RT-qPCR failed to produce a positive result.

Point-of-use (POU) NAA for environmental surveillance normally requires the implementation of complex procedures required for sample preparation, including viral particle concentration, RNA extraction, and subsequent purification. For RNA concentration and purification, specialized commercial kits for environmental samples are commonly employed, but they involve a series of manual operations. These sample preparation steps take may take more than two hours and require specialized instruments. Thus, integration of sample preparation is highly desirable for the implementation of rapid, sensitive, and POU quantification platforms targeting microorganisms in environmental or wastewaters.

Accordingly, a rapid, simplified, low-cost system and method for detecting microbes is desirable to deliver the benefits of sensitive molecular assays in situations requiring POU field testing of environmental water or wastewater in places with limited resources.

SUMMARY

Alternative to PCR-based NAA techniques, isothermal amplification methods, such as loop mediated isothermal amplification (LAMP), offer the opportunity to deliver the benefits of molecular assays beyond centralized laboratories. With no need for thermal cycling, LAMP isothermal reactions are more suitable to be coupled with miniaturized, portable, and battery-powered platforms. Initially described in 2000, LAMP has become a popular isothermal amplification technique covering important microbial pathogens.

Disclosed herein are examples of one or more membrane-based, in-gel loop-mediated isothermal amplification (mgLAMP) methods, kits, and systems for detecting target microorganisms (including viral particles, bacterial cells, or target DNA/RNA) in samples, e.g., environmental waters or wastewaters, suspected of containing the target microorganisms.

In some embodiments, the system, kit, and/or method is for absolute quantification of SARS-CoV-2 in environmental water samples within a one-hour timeframe. The limit of detection (LOD) was 0.96 copy/mL in Milli-Q water and 93 copies/mL in surface water. The mgLAMP techniques of these embodiments and their performance was characterized in SARS-CoV-2 spiked Milli-Q water, river water samples, and wastewater samples. In some embodiments, POU applications of the mgLAMP systems and methods may be facilitated by a portable device that integrates heat incubation, fluorescence illumination, and a cloud-based smartphone image analysis algorithm for quantitative results interpretation. The integrated portable platform can be reliably used for the POU absolute quantification of SARS-CoV-2 in environmental water samples.

The disclosed mgLAMP systems, kits and/or methods, as NAA-based platforms, may also be adapted for the detection of other microbial pathogens and can be modified for use in other sample matrices (e.g., clinical samples). While the disclosed exemplary embodiments may focus on SARS-CoV-2 detection, the mgLAMP techniques can also be adapted for the detection and/or monitoring of other microbial pathogens (e.g., *E. coli, Salmonella*) in water or samples in other settings, e.g., clinical settings. The systems, kits and/or methods may also be configured for microorganism detection and quantification in other matrixes (e.g., food, feces, urine, and blood).

In accordance with an exemplary embodiment, a system for detecting a target microorganism in a sample suspected of containing the target microorganism includes at least one primary filter configured to remove particles larger than a target microorganism from a sample. A downstream filter membrane receives the primary filtered sample and traps one or more of the target microorganism, if present, on a membrane, while passing through the membrane particles present in the primary filtered sample that are smaller than the target microorganism. A slide receives the membrane after it has filtered the sample. Loop mediated isothermal amplification (LAMP) reagents and hydrogel components for forming a hydrogel are also included. The LAMP reagents and the hydrogel components are placed on the membrane to form a loaded slide. A film is included for sealing the loaded slide. An incubator is configured to heat the sealed, loaded slide; and a fluorescence illuminator is provided to illuminate the sealed, loaded slide.

The slide allows visual detection of the presence or absence of one or more fluorescent amplicons that are produced as a result of a LAMP reaction amplifying the DNA/RNA of the target microorganism, if the target microorganism is present on the membrane. The presence of the amplicons is indicative of the presence of the target microorganism in the sample and the absence of the amplicons is indicative of the absence of the target microorganism in the sample.

In accordance with another exemplary embodiment, a method of detecting a target microorganism in a sample suspected of containing the target microorganism includes: filtering a sample to remove particles larger than the target microorganism from the sample; and filtering the primary filtered sample with a filter membrane configured to trap the target microorganism, if present, on a membrane, while passing through the membrane particles in the sample that are smaller than the target microorganism, whereby producing a loaded membrane. Loop mediated isothermal amplification (LAMP) reagents and hydrogel components for forming a hydrogel are combined into a mixture. The loaded membrane is applied to a slide. The mixture is then applied to the loaded membrane after the membrane is placed on the slide to form a loaded slide. The loaded slide is sealed with a film. The hydrogel polymerizes over a short time to immobilize the targets within the mixture. The sealed, loaded slide is then incubated. After incubation, the sealed, loaded, slide is illuminated with a fluorescence illuminator.

The target is detected by visual inspection for the presence or absence of one or more fluorescent amplicons on the sealed, loaded, incubated slide. The amplicons are produced as a result of a LAMP reaction amplifying the DNA/RNA of the target microorganism, if the target microorganism is present on the membrane. The presence of the amplicons is indicative of the presence of the target microorganism in the sample and the absence of the amplicons is indicative of the absence of the target microorganism in the sample. The target concentrations may be determined based on the number of fluorescent amplicon dots after the reaction using a smartphone.

The foregoing summary does not define the limits of the appended claims. Other aspects, embodiments, features, and advantages will be or will become apparent to one with skill in the art upon examination of the following figures and detailed description. It is intended that all such additional features, embodiments, aspects, and advantages be included within this description and be protected by the accompanying claims.

BRIEF DESCRIPTION OF THE FIGURES

It is to be understood that the drawings are solely for purpose of illustration and do not define the limits of the appended claims. Furthermore, the components in the figures are not necessarily to scale. In the figures, like reference numerals designate corresponding parts throughout the different views.

DETAILED DESCRIPTION

Figure 1:
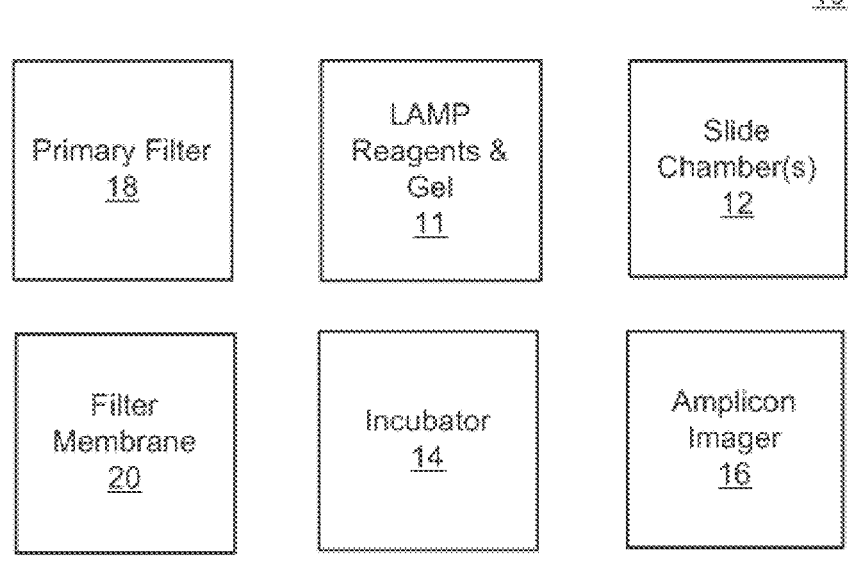
FIG. 1 is a schematic illustration of an exemplary membrane-based in-gel LAMP (mgLAMP) assay system.

The following detailed description, which references to and incorporates the drawings, describes and illustrates one or more examples of assay systems, kits, devices, and methods based on membrane-based, in-gel loop-mediated isothermal amplification (mgLAMP) to test samples. These examples, offered not to limit but only to exemplify and teach embodiments of inventive assays, systems, kits and methods, are shown and described in sufficient detail to enable those skilled in the art to practice what is claimed. Thus, where appropriate to avoid obscuring the invention, the description may omit certain information known to those of skill in the art. The disclosures herein are examples that should not be read to unduly limit the scope of any patent claims that may eventual be granted based on this application.

The word "exemplary" is used throughout this application to mean "serving as an example, instance, or illustration." Any system, method, device, technique, feature or the like described herein as "exemplary" is not necessarily to be construed as preferred or advantageous over other features.

As used in this specification and the appended claims, the singular forms "a," "an," and "the" may include plural referents unless the content clearly dictates otherwise.

Although any methods and materials similar or equivalent to those described herein can be used in the practice or testing of the invention(s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The terms "microorganism," "microbial" or "microbes" as used herein includes bacteria, fungal, protozoal, and viral organisms. The methods and system of the disclosure can be used to detect and identify the presence of such microbial organisms.

Bacterial microbes that can be detected using the kits, methods and systems of the disclosure include both gram-negative and gram-positive bacteria. For example, bacteria that can be affected include *Staphylococcus aureus, Streptococcus pyogenes* (group A), *Streptococcus* sp. (*viridans* group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus mirablis* and other sp., *Pseudomonas aeruginosa, Klebsiella pneumoniae, Salmonella, Shigella, Serratia*, and *Campylobacter jejuni*. In particular, the methods and systems of the disclosure are useful for detection of any pathogen. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections.

Fungal organisms may also be detected by the methods and system of the disclosure, e.g., *Microsporum canis* and other *Microsporum* sp.; and *Trichophyton* sp. such as *T. rubrum*, and *T. mentagrophytes*, yeasts (e.g., *Candida albicans, C. Tropicalis*, or other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* sp., *Zygomycetes*

(e.g., *Rhizopus, Mucor*), *Paracoccidioides brasiliensis, Blastomyces dermatitides, Histoplasma capsulatum, Coccidioides immitis*, and *Sporothrix schenckii*.

Viral organisms that can be detected by the method and systems of the disclosure include, but is not limited to, SARS-CoV-2 virus, human immunodeficiency virus (HIV), Junin Virus, BK virus, Machupo virus, Varicella zoster virus, alphavirus, Colorado tick fever virus, rhinoviruses and coronaviruses, cytomegalovirus, Dengue viruses, Ebolavirus, Enterovirus sp., Herpes simplex-1, -2, Hepatitis-A, -B, -C, -D, -E viruses, Measles virus, Mumps virus, Norovirus, respiratory syncytial virus, Rotavirus, Rubella virus, SARS coronavirus, West Nile Virus and Zika Virus.

While the disclosed exemplary embodiments may focus on SARS-CoV-2 detection, the mgLAMP techniques can also be adapted for the detection and/or monitoring of other target microbial pathogens, such as those identified above, in water, clinical or food samples. In addition to environmental waters and wastewaters, the kits, systems and methods disclosed herein may be used for target microorganism detection and quantification in other matrixes (e.g., food, feces, urine, and blood).

The pandemic of coronavirus disease 2019 (COVID-19) is predicted to become endemic with seasonal fluctuations. The SARS-CoV-2 virions and their RNA are known be shed in feces of infected individuals at a concentration of $10^2$ to $10^8$ copies/g. Depending on sanitary practices, the viral RNA is commonly discharged in wastewater and surface waters. Detection of SARS-CoV-2 RNA in river water and wastewater has been widely reported globally such as in Italy, Japan, and Brazil. In Spain, SARS-CoV-2 RNA was detected in wastewater before the first local case was confirmed. Virions may persist in environmental waters given that the time required for 99% viable virus load reduction ($T_{99}$) of 19.5 days for wastewater and $T_{99}$ at 18.7 days for river water at 4° C. Thus large-scale environmental surveillance is desirable for quantitative risk assessment, for notice of potential outbreaks, population-wide infection prevalence monitoring, and for a better understanding of SARS-CoV-2 contamination and potential spread via environmental waters. Therefore, the point-of-sampling testing technologies disclosed herein are useful for large-scale environmental surveillance because they reduce or avoid the use of specialized equipment, highly-trained personnel, and labor-intensive laboratory procedures.

Detection of SARS-CoV-2 may be based on nucleic acid analysis (NAA) using primarily reverse transcription quantitative polymerase chain reaction (RT-qPCR). RT-qPCR is not readily adaptable for large-scale environmental surveillance especially in resource-limited settings due to its requirement for a specialized thermocycling instrument and the need for highly-trained personnel. Furthermore, RT-qPCR does not produce absolute quantification. In addition, RT-qPCR targeting SARS-CoV-2 is sensitive to inhibitors that are present in wastewater leading to false negative results. To address these challenges, isothermal NAA methods, such as loop-mediated isothermal amplification (LAMP), may be used for environmental quantification of other microbial pathogens including Zika virus, astrovirus, MS2, *E. coli*, and *Enterococcus* spp. RT-LAMP quantification has higher tolerances to inhibitors and shorter the amplification times (e.g., 30 minutes) compared to RT-qPCR. A portable in-gel LAMP platform has previously been used for the sensitive detection of MS2 coliphage in wastewater. RT-LAMP has also been used in portable SARS-CoV-2 detection platforms for use on clinical samples. However, isothermal methods have yet to be developed for detecting SARS-CoV-2 in environmental water samples.

RT-LAMP reactions include a reverse transcriptase and a DNA polymerase with strong strand displacement activity and tolerance for elevated temperatures and up to six DNA oligonucleotides of a certain architecture. Samples with potential template molecules are added to the reaction and incubated for 10 to 60 min at a constant temperature (e.g., 65° C.). Accordingly, a specialized thermocycler is not needed, only a heat block. The oligonucleotides act as primers for the reverse transcriptase, and additional oligonucleotides for the DNA polymerase are designed so the DNA products loop back at their ends. These, in turn, serve as self-priming templates for the DNA polymerase. In the presence of a few RNA template molecules, a chain reaction is set in motion, which then runs until the added reagents (in particular, the deoxynucleotide triphosphates) are used up. LAMP exhibits increased sensitivity and specificity due to an exponential amplification feature that utilizes 6 different target sequences simultaneously identified by separate distinct primers in the same reaction. LAMP assays are significantly rapid, and do not require expensive reagents or instruments, which aids in cost reduction for coronavirus detection.

The LAMP system principally employs four core primers, namely FIP (forward inner primer), BIP (backward inner primer), F3 (forward primer) and B3 (backward primer) to recognize six different regions of the target sequences. First, FIP anneals to the template, and extension occurs using a polymerase with displacement activity (such as a Bst polymerase), the product obtained from FIP is then displaced by the extension reaction associated with the F3 primer. Subsequently, an extension reaction occurs using BIP on the product of FIP, and not on the template DNA due to displacement by DNA synthesis associated with the B3 primer. These reactions result in a product with a dumbbell-like structure which is essential for LAMP to establish isothermal amplification as the loop structures are always single stranded and can be annealed by FIP or BIP. This loop structure formation eliminates the denaturing step, which is otherwise essential in PCR for obtaining single-stranded DNA, and also establishes a cyclic reaction between the dumbbell-like structure and its complementary product, leading to elongated products with various copies of the target sequence produced. Two optional primers, LF (loop forward) and LB (loop backward), can be added to the amplification reaction to enhance the reaction speed. This modification, also known as "accelerated LAMP", was a later modification of the classical, four-primer LAMP. Though the exact mechanism is unclear, the LF/LB primers presumably accelerate the four primer LAMP reaction by creating additional binding sites for the auto-cycling FIP/BIP primers. The auto-cycling leads to the formation of "cauliflower-like" DNA structures, which essentially are DNA concatemers with loops interspersed between alternating inverted repeats. Formation of these multimeric products of the target region represents a successful amplification of the target DNA. LAMP is an ultrasensitive nucleic acid amplification method that can detect minute quantities of DNA or RNA templates within roughly an hour, far outstripping normally utilized RT-PCR methods, particularly with the current demands for rapid and sensitive testing.

Typically, the measurement of LAMP products relies on end-point analysis and requires post-amplification processing, leading to possible cross-contamination or detection of non-specific LAMP amplicons. Some of these methods include: resolving amplified products on agarose gel electrophoresis' turbidity analysis of positive reactions due to the accumulation of magnesium pyrophosphate ($Mg_2P_2O_7$), detection of dsDNA under UV-light in presence of an intercalating dyes like SYBR Green I or EvaGreen and addition of metal ion indicators like, calcein/$Mn^2$ and hydroxynapthol blue dye (HNB). Amongst these, the use of intercalating fluorescent dyes has been favored for clinical diagnostics as they are more sensitive and relatively tolerant towards opaque substances like proteins, which are known to affect turbidimetric signal. A major disadvantage, however, of using non-specific detection methods is the increased likelihood of detecting false positives. This is despite the fact that LAMP relies on 4-6 different primers to independently recognize 6-8 independent regions on the target sequence suggesting, at least in theory, a higher degree of specificity than a two-primer PCR. Though the mechanism of non-specific amplification remains unclear, it is assumed that cis and trans priming amongst the six primers, could be responsible for this phenomenon. Thus, indirect detection of amplification products remains one of major shortcomings of LAMP technology.

A modified LAMP assay that incorporates a primer or probe which is labelled with a label (e.g., a fluorophore) can be used in order to monitor or determine amplicon formation. Examples of such modified LAMP assays, include LAMP assays which incorporate one of the following techniques: fluorescence of loop primer upon self-dequenching (FLOS) LAMP, HyBeacon probes, Guanine quenching principle, alternately binding quenching probe competitive LAMP (ABC-LAMP), fluorophore-modified primer with ethidium bromide, universal quenching probe (QProbe), and graphene oxide (GO) based FRET. In another embodiment, the LAMP assay disclosed herein is a modified LAMP assay that incorporates multiple primers or probes that are labelled with labels (e.g., fluorophore(s), FRET pairs, and/or quencher(s)) in order to monitor or determine amplicon formation. Examples of such modified LAMP assays, include LAMP assays which incorporate one of the following techniques: detection of amplification by release of quenching (DARQ), quenching of unincorporated amplification signal reporters (QUASR), toehold-mediated strand exchange reaction, termed one-step strand displacement (OSD), molecular beacon, lightCycler, assimilating probe, and mediator displacement (MD) LAMP. The specifics for each of the following techniques can be found in Becherer et al. (Anal. Methods, 12:717-746 (2020), the disclosure of which is incorporated herein in-full.

Fluorophore labelled nucleic acids that specifically hybridize, in a sequence dependent manner, to a transiently generated single-stranded DNA structure, have proven to be an ideal solution to any non-specific, dye-based detection system. Examples of such include the, hydrolysis-based TaqMan™ probes specifically developed for qPCR and molecular beacons among host of others. Due to the atypical amplification chemistry of iNAAT's and LAMP per se, seamless application of any of these probe technologies, specifically developed for qPCR have proven to be technically challenging. Attempts however have been made to develop a probe-based detection system for LAMP include: loss-of-signal guanine quenching, gain-of-signal fluorescence using labeled primers, detection of amplification by release of quenching (DARQ), assimilating probe, one-step-toe-hold (OSD) reporter and more recently, molecular beacons. The use of self-quenching fluorogenic probes as an alternative approach to detect and monitor LAMP reactions in real-time has been recently developed and is termed Fluorescence of Loop Primer Upon Self Dequenching-LAMP (FLOS-LAMP). The FLOS-LAMP utilizes a labelled loop probe quenched in its unbound state, fluoresces only when bound to its target (amplicon). For the LAMP reactions, the fluorophore is conjugated internally to the primer sequence, not on the end, and the expected fluorescent property of primary and secondary deoxyoligonucleotide structure can change (10-fold) upon hybridization. The FLOS probe can comprise different fluorophores (FAM, JOE and ROX), enhancing the versatility of the assay.

Any non-dumbbell shaped nucleic acid structure(s) that are presumably formed in a typical LAMP reaction, is unable to offer a binding site to the FLOS-probe. As a result, no spurious signal gets generated. This is a major technical advancement considering the fact that the majority of the real-time LAMP assays used in clinical diagnostics use the in-direct detection approach (e.g. intercalating dyes) which cannot discriminate between a genuine amplicon and background. As a result, some form of additional, post-amplification, confirmatory step is usually implemented, for e.g. dissociation curve analysis, to confirm the veracity of the detected signal. Such post-amplification analysis can be a challenge to implement especially in a POC setting, where any unreasonable complications to interpret the data can negatively affect the turnaround time. The use of FLOS-LAMP obviates such post-amplification processing, resulting in greater simplicity as well as accuracy.

Point-of-use (POU) NAA for environmental surveillance normally requires the implementation of complex procedures required for sample preparation, including viral particle concentration, RNA extraction, and subsequent purification. SARS-CoV-2 loads observed in surface water and wastewater are typically lower than the detection limit of RT-qPCR. Therefore, using conventional practices, SARS-CoV-2 viral particles are typically concentrated from 50-500 mL water sample for example by ultracentrifugation, ultra-filtration, polyethylene glycol (PEG) precipitation, or electronegative membrane filtration. The recovery rates using these methods for SARS-CoV-2 concentration of samples taken from wastewater and surface waters are poorly understood, while the recovery rates for similar-structured surrogates are generally in the range of 26.7-65.7%. Other existing in-field virus concentration technologies, such as nanofiltration via superabsorbent polymer microspheres and bag-mediated filtration, may be adaptable for SARS-CoV-2. For RNA concentration and purification, specialized commercial kits for environmental samples are commonly employed but they involve a series of manual operations. These sample preparation steps take at least two hours and require specialized instruments. Integration of sample preparation is thus needed for the development of rapid, sensitive, and POU quantification platforms targeting SARS-CoV-2 in environmental waters.

FIG. 1 is a schematic illustration of an exemplary membrane-based in-gel LAMP (mgLAMP) assay system 10, which may enable target microbial pathogen detection and quantification, e.g., SARS-CoV-2 quantification, within about 60 minutes. The system 10 may include a kit that includes a primary filter 18, a filter membrane 20 for catching target microorganism particles, LAMP reagents and polymer gel components 11, and one or more chambers 12 that include at least one slide for viewing a mixture of the LAMP reagents, gel and sample placed on the filter membrane 20. The system 10 may also include an incubator 14 for heating the mixture/membrane 20 placed on the slides;

and an imager 16 for viewing the amplification products, e.g., amplicon dots, resulting from the LAMP reaction in the chamber(s) 12.

The primary filter 18 may be any suitable filter for removing particles larger than the target microorganism, such as impurities, from the sample. An example primary filter 18 is described herein in connection with FIG. 10.

The filter membrane 20 may be any porous membrane configured to trap the target microorganism on the membrane surface, if present in the sample, while passing particles in the sample that are smaller than the target microorganism. For example, the filter membrane 20 may be a membrane with pore sizes between 50 nm and 200 nm, for example, a membrane having a pore size of 50, 80, 100, or 200 nm, and in some embodiments, pore sizes of 80 nm or less. In some embodiments, the filter membrane may be a porous track-etched polycarbonate (PCTE) membrane, for example, a PCTE membrane (ø13 mm) with a pore size selected from 50, 80, 100, or 200 nm, available from Sterlitech Corporation (Kent, WA).

In some embodiments, the filters 18 and 20 may be the filter system 400 shown and described in connection with FIG. 10.

The LAMP reagents 11 may include, consist of, or consist essentially of any suitable LAMP reagents for initiating and completing a LAMP reaction, for example, those described herein below. For example, the LAMP reagents may include a predefined set of RT-LAMP (reverse-transcription LAMP) primers targeting various regions in the target microorganism genome. Quenching of Unincorporated Amplification Signal Reporter (QUASR) quencher probes corresponding to the RT-LAMP primers may also be included. In some embodiments, a lysing agent may be included with the reagents 11 in the kit, for example, any of those disclosed herein below.

The polymer gel 11 may be a hydrogel for forming a gel matrix that restricts dispersion of the target microorganism, LAMP reagents, and/or inhibitors present in the sample when mixed together. The specific concentration, type and formulation of the hydrogel may be selected such that the detection results produced by system 10 are enhanced. The hydrogel may include, consist of, or consist essentially of any suitable polymer gel or combinations of different gels. For example, in some exemplary embodiments, the polymer gel acting as the matrix for mgLAMP may be a polyacrylamide gel. In other exemplary embodiments, the polymer gel acting as the matrix for mgLAMP may be a polyethylene glycol (PEG) hydrogel. For example, a PEG gel may be formed through Michael addition between the four-arm PEG acrylate (molecular weight (MW) 10K) and thiol-PEG-thiol (MW 3.4K) (Laysan Bio, Arab, AL) at mole ratio of 1:2.

The hardware included in the system 10 may include standard laboratory devices, in some embodiments. The slide chamber 12 may include any suitable chamber for holding and viewing the mixture loaded on the filter membrane 20, for example, a PCR frame seal chamber. The incubator 14 may be any suitable means for heating the mixture for the desired period of time at the desired temperature(s). For example, the incubator 14 may include a commercially-available PCR machine or a mini dry bath. Alternatively, a simple water bath may be used as a heat source for the incubator 14 in some instances. And in some embodiments, the incubator 14 may be part of the integrated portable devices 200, 300 (FIGS. 4-9) as disclosed herein. The amplicon imager 16 may include any suitable means for visually inspecting the processed mixture on the loaded membrane; for example, the imager 16 may include a fluorescent illumination source and a camera or fluorescent microscope for capturing images of the illuminated slide presenting the processed mixture/membrane. For example, the illumination source may be one or more inexpensive blue (460-470 nm) LEDs, UV LEDs, and/or white LEDs (with a blue passing filter) or an LED array used to illuminate the slides or a gel imager. Also, the illumination source may be any of those included in the integrated portable devices 200, 300 (FIGS. 4-9) disclosed herein.

Considering its simplicity, sensitivity, and rapidity, the mgLAMP system 10 presents a vastly improved technique for microbial water quality analysis, especially in resource-limited settings. The mgLAMP assay system 10 may also be useful for other water testing/monitoring applications or food sample applications.

Figure 2:
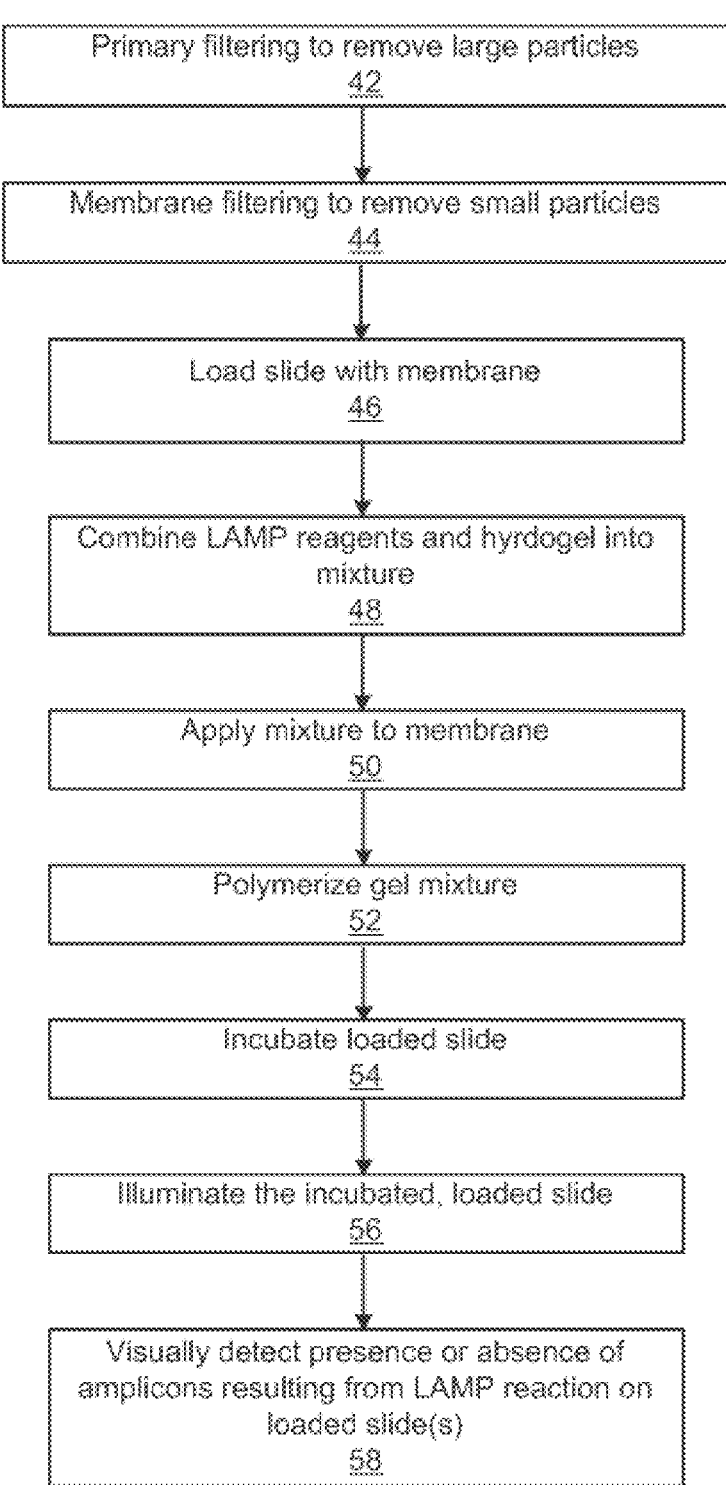
FIG. 2 is a flowchart diagram illustrating an exemplary mgLAMP method of detecting a microorganism in a sample.

FIG. 2 is a flowchart diagram illustrating an exemplary mgLAMP method 40 of detecting a target microorganism in a sample, which may employ the system 10. Generally, during operation of the assay system 10, filtered target microorganisms are immobilized with LAMP reagents within a polymer gel, for example, a hydrogel such as one or more polyethylene glycol (PEG) hydrogels on a filter membrane, and then the viral RNAs are amplified through an in situ LAMP reaction. Due to the restriction effect of the polymer gels, one target microorganism may only produce one amplicon dot. Therefore, the sample microorganism concentrations can be determined based on the number of fluorescent amplicon dots after the reaction using the amplicon imager 16, e.g., smartphone or a fluorescent microscope.

Referring to the flowchart, in step 42, a sample undergoes primary filtration to remove particles larger than the target microorganism from the sample. The primary filter 18 may be any suitable filter for accomplishing this task, including the filter 400 described herein in connection with FIG. 10. The sample may be an environmental sample or clinical sample. For example, the sample include environmental water, wastewater, soil, feces, urine, blood, or any combination of the foregoing.

Next, in step 44, the primary filtered sample is filtered with the filter membrane 20, which is configured to trap the target microorganism, if present, on the filter membrane 20, while passing through the membrane 20 particles in the sample that are smaller than the target microorganism. This step resulting in a loaded membrane. In step 46, the loaded membrane is placed on a slide.

In step 48, loop mediated isothermal amplification (LAMP) reagents and the hydrogel components for forming a hydrogel are combined into a mixture. The LAMP reagents include any of the reagents disclosed herein.

The hydrogel may include, consist of, or consist essentially of any suitable polymer gel or combinations of different gels, including any of those disclosed herein. For example, in some exemplary embodiments, the polymer gel acting as the matrix for mgLAMP may be a polyacrylamide gel. In other exemplary embodiments, the polymer gel acting as the matrix for mgLAMP may be a polyethylene glycol (PEG) hydrogel. For example, a PEG gel may be formed through Michael addition between the four-arm PEG acrylate (molecular weight (MW) 10K) and thiol-PEG-thiol (MW 3.4K) (Laysan Bio, Arab, AL) at mole ratio of 1:2.

In step 50, the mixture is then applied to the loaded membrane after the membrane is placed on the slide to form a loaded slide. The loaded slide is then sealed with a film. The hydrogel polymerizes over a short time to immobilize the targets within the mixture (step 52). The sealed, loaded slide is then incubated (step 54). After incubation, the sealed, loaded, slide is illuminated with a fluorescence illuminator (step 56).

In step 58, the target is detected by visual inspection for the presence or absence of amplification products, e.g., one or more fluorescent amplicons on the sealed, loaded, incubated slide. The amplicons are produced as a result of a LAMP reaction amplifying the DNA/RNA of the target microorganism, if the target microorganism is present on the membrane. The presence of the amplicons is indicative of the presence of the target microorganism in the sample and the absence of the amplicons is indicative of the absence of the target microorganism in the sample. The target concentrations may be determined based on the number of fluorescent amplicon dots after the LAMP reaction using a smartphone or other means such as a fluorescent microscope.

Figure 3:
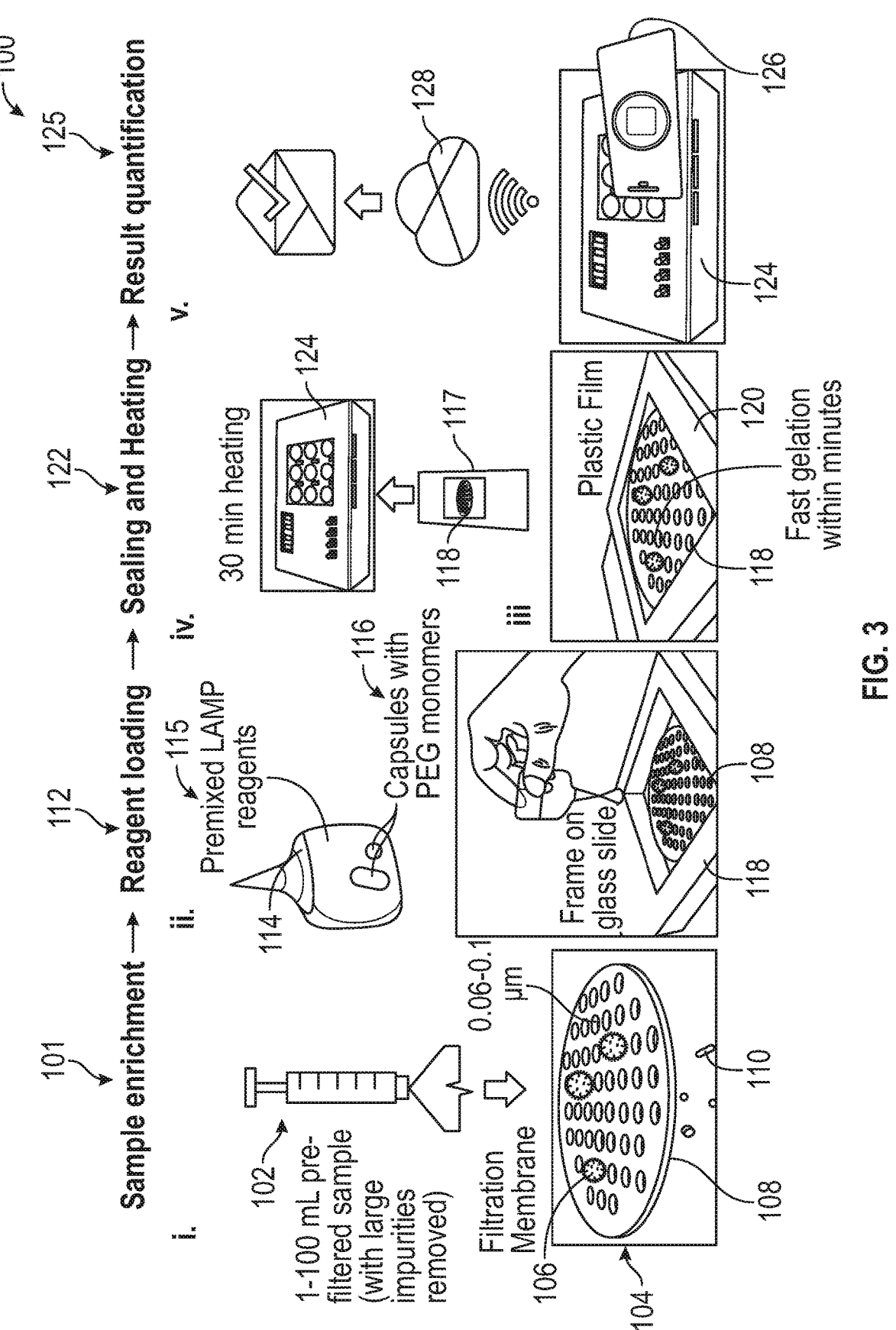
FIG. 3 is an additional schematic diagram of an exemplary mgLAMP process of detecting a microorganism in a sample.

FIG. 3 is an additional schematic diagram of an exemplary mgLAMP process 100 of detecting a target microorganism in a sample. The process 100 illustrates specific use of the kits, devices, and systems disclosed herein for absolute quantification of the SARS-CoV-2 virus in environmental water samples within a one-hour timeframe.

Experimental testing of the process 100 demonstrated that the limit of detection (LOD) was 0.96 copy/mL in Milli-Q water and 93 copies/mL for SARS-CoV-2 in surface water. Its performance was characterized in SARS-CoV-2 spiked Milli-Q water, river water samples, and wastewater samples. Also demonstrated was the feasibility of point-of-use (POU) applications by using the portable integrated devices (PIDs) disclosed herein that integrate heat incubation, fluorescence illumination, and a cloud-based smartphone image analysis algorithm for quantitative results interpretation. Experimentation demonstrated that the integrated portable platform can be reliably used for the POU absolute quantification of SARS-CoV-2 in environmental water samples. The mgLAMP process 100, as an NAA-based platform, may also be adapted for the detection of other microbial pathogens and can be modified for use in other sample matrices (e.g., clinical samples, food, blood, urine, feces, any combination of the foregoing, or the like).

The workflow of the process 100 for analysis of a water sample containing SARS-CoV-2, as an example, is shown in FIG. 3, from sample-in to result-out.

To experimentally establish efficacy of the process 100, surface water samples were collected from a suburban river in the Godawari Botanical Garden, Godawari Khola, Nepal. Also, wastewater samples, including raw influent samples and primary effluent samples, were collected from a water reclamation plant serving a population of approximately one million people. Total dissolved solids (TSS) concentration of each water sample was determined according to Standard methods 2540 D by filtering a 20-mL water volume through a TSS glass fiber filter (pore size 1.5 μm, diameter 47 mm, available from Hach Company, Loveland, CO) and weighing the 104° C.-dried residues. Dynamic light scattering (DLS) measurements were conducted using NanoBrook ZetaPALS and its accompanied software (Brookhaven Instruments, Holtsville, NY) for environmental samples before and after virus dislodging. Each sample of 200 μL was homogenized before DLS measurement by manual shaking and was loaded into a disposable cuvette (available from Eppendorf, Hamburg, Germany). The particle size distribution was analyzed in the software with an angle of 90°, a wavelength of 659.0 nm, and a refractive index of 1.330.

Inactivated SARS-CoV-2 strains from the American Type Culture Collection (ATCC® VR-1986HK®, $1.92\times10^5$ copies/μL, Manassas, VA) and ZeptoMetrix (NATSARS (COV2)-ST, $9.3\times10^5$ copies/mL, Buffalo, NY) were used during testing to spike the sample waters.

The first phase of the example mgLAMP process 100 includes sample enrichment 101 to concentrate and purify the target microorganism, e.g., the Covid-19 virus, from a sample. Raw environmental or wastewater samples inevitably contain varying size of particles and a variety of complex chemical and biological components that may inhibit amplification. Before surface water and wastewater samples are analyzed by mgLAMP, target particles, e.g., SARS-CoV-2 particles, are detached from aggregated suspended solids through a dislodging process in which large particles including sand and plankton are blocked out and removed by either one or two tiers of pre-filtration, before reaching the 80-nm PCTE filter membrane, as described in connection with FIG. 10.

Initially, a 1-100 mL sample is pre-filtered (step 102) using a two-tier primary filter such as the filter 400 shown and described in connection with FIG. 10. The pre-filtering removes larger particles, e.g., those larger that the target, from the sample. In experimental testing, TSS values of surface water, raw influent, and primary effluent were separately determined to be 430.00 mg/L, 99.58 mg/L, and 55.12 mg/L, respectively. DLS analysis results revealed that particle size in surface water was observed to be relatively uniform at a size close to 500 nm, which is larger than the size of the SARS-CoV-2 virus. Raw wastewater influent and primary effluent had particle sizes ranging from 180.8 nm to 7582.5 nm, which made it easier to separate SARS-CoV-2 particles from other larger particles in surface water. Therefore, in some embodiments, such as those processing surface water, the tiered-pre-filtration may be simplified, i.e., the $2^{nd}$ tier filtering may be omitted; whereas in other embodiments, i.e., in the case of raw influent and primary effluent, two tier filtering is used.

Next, smaller and potentially inhibitory molecules are filtered out (step 104). This filtering may be accomplished using a porous track-etched polycarbonate (PCTE) membrane 108, as described herein, that contains pores between 0.06-0.1 μm, for example, about 80 nm to retain the SARS-CoV-2 virus particles 106, while allowing smaller particles and molecules 110 to pass. Such PCTE membranes are available from Sterlitech Corporation (Kent, WA). The eliminated molecules 110 may include dissolved organic or inorganic matters, salts, and inhibitors to the RT-LAMP reaction, such as humic acids and heavy metals. PCTE membranes are generally capable of microorganism concentration from complex matrices and compatible with LAMP reactions.

The filter membrane 20, 108 functions both as a filter that retains target viral particles and as a carrier for direct RT-LAMP analysis. Selection of an appropriate pore size of the membrane plays a role in establishing the mgLAMP efficacy, since viral capture may be based on size exclusion. SARS-CoV-2 is an enveloped spherical virus, with the diameter ranged from 60 to 140 nm and spikes protruding 9 to 12 nm. Considering possible aggregation of viral particles, PCTE membranes with pore sizes of 50, 80, 100, and 200 nm were compared for their recovery rates of spiked SARS-CoV-2 in Milli-Q water. To test various pore sizes, 1-mL Milli-Q water (Milli-Q, Millipore, Billerica, MA) spiked with $1.92\times10^5$ copies/mL ATCC SARS-CoV-2 particles was filtered through each PCTE membrane on top of a 13-mm PETE drain disc using a disposable 13-mm Swinnex filter holder (Sigma-Aldrich, St. Louis, MO) by hand.

For SARS-CoV-2, membranes with 80-nm pores captured the most viral particles, allowing for employment in the mgLAMP system for experimental testing. An 80-nm pore PCTE membrane on top of a 13-mm PETE drain disc (Sterlitech Corporation, Kent, WA) using a disposable 13-mm Swinnex filter holder may be used with hand pumping. The PETE drain disc was used as a mesh spacer to avoid the PCTE membrane damage during high pressure or fast flow condition, and to allow the even distribution of target cells on the PCTE membrane.

Testing results show that viruses were mostly dispersed individual particles. The absence of severe viral particle aggregation may facilitate more accurate LAMP analysis by providing ample separation among the amplicon dots. Larger pore sizes may allow more virus particles to slip through, leading to a lower recovery efficiency. The smallest pore size tested (50 nm) may retain the most viral particles, but higher pressures may build on the membrane due to reduced flow reduction and possible pore blockage. For viruses with an enveloped structure similar to SARS-CoV-2, high pressures may induce conformational changes that shrink the virus particle volume or even displace the spike proteins. This may result in viral particles squeezing through the membrane pores and evading analysis.

Next, reagent loading 112 is performed. In some embodiments, the mgLAMP reagents may be contained in an openable plastic reagent pouch 114 containing premixed LAMP reagents 115 and a lysis agent in liquid form, along with one or more breakable capsules 116 containing a dry, powder form of the hydrogel components, such as PEG monomers. In some embodiments the hydrogel components may be liquid. The plastic pouch 114 may be made of any suitable, flexible non-reactive plastic, such as polyethylene or polypropylene, that may form a squeezable bag that allows a user to break the capsules internally and thus mix the LAMP reagents, the lysis agent, and the hydrogel components in the pouch to form a mixture. The pouch can then be manually opened by tearing or cutting to apply the mixture to the membrane 108 while fixed in the slide frame 118, as shown in FIG. 3. The capsules may be plastic or glass capsules that encapsulate the hydrogel components.

In some embodiments, the RT-LAMP reagents may be for a 30-μL mgLAMP reaction. The mixture may contain 5% (w/v) hydrogel, 15 μL of 2× WarmStart LAMP Master Mix, 0.5% Triton X-100 (as a lysis agent), 1 U/μL RNase Inhibitor Murine (NEB, Ipswich, MA), 0.02 U/μL Antarctic Thermolabile UDG (NEB, Ipswich, MA), 700 μM dUTP (NEB, Ipswich, MA), 1.6 μM FIP and 5' FAM-BIP, 0.2 μM F3 and B3, 0.4 μM LB, 2.4 μM qBIP15nt, and nuclease-free water. The reagents may contain Triton X-100 for in-assay viral lysis. The PEG hydrogel may be formed through thiol-Michael addition reaction between 4-arm PEG acrylate (molecular weight (MW) of 10 K, Biochempeg, Watertown, MA) and thiol-PEG-thiol ($SHCH_2CH_2O(CH_2CH_2O)_nCH_2CH_2SH$) (MW of 3.4 K, Laysan Bio, Arab, AL) at a molar ratio of 1:2. As the RT-LAMP reaction vessel, PEG hydrogel has high tolerance to environmental inhibitors by limiting their diffusion, while large amount of amplification products are generated. The target-specific QUASR probe facilitates fluorescence amplicon dot formation in the hydrogel. The foregoing reagents and components may be placed in a squeezable pouch, as described previously herein.

In some embodiments, the RT-LAMP reagents, mix components, and concentrations may be those shown in Table 1.

The reagents and components may be placed in a squeezable pouch, as described previously herein. The primer sequences and QUASR sequences for this embodiment are shown in Tables 2 and 3, respectively.

TABLE 1

| Component | [ ]. Final | Unit |
|---|---|---|
| 4 arm PEG-acrylate, MW 10K | 5 | w/v % |
| (Biochempeg, Watertown, MA, USA) | | |
| thiol-PEG-thiol, MW 3,400 | 5 | w/v % |
| (Laysan Bio Inc., Arab, AL, USA) | | |
| WarmStart LAMP 2X Master Mix | 1 | x |
| (E1700, NEB Inc., Ipswich, MA, USA) | | |
| RNase Inhibitor, Murine | 1 | U/μL |
| (M0314, NEB Inc., Ipswich, MA, USA) | | |
| Triton X-100 | 0.5 | v/v % |
| (T8787, Sigma Aldrich, St. Louis, MO, USA) | | |
| Antarctic Thermolabile UDG | 0.02 | U/μL |
| (M0372, NEB Inc., Ipswich, MA, USA) | | |
| dUTP Solution | 700 | μM |
| (N04595, NEB Inc., Ipswich, MA, USA) | | |
| F3 (IDT, Inc., Coralville, IA, USA) | 0.2 | μM |
| B3 (IDT, Inc., Coralville, IA, USA) | 0.2 | μM |
| FIP (IDT, Inc., Coralville, IA, USA) | 1.6 | μM |
| FAM-BIP (IDT, Inc., Coralville, IA, USA) | 1.6 | μM |
| LB (IDT, Inc., Coralville, IA, USA) | 0.4 | μM |
| BIPc-17nt (IDT, Inc., Coralville, IA, USA) | 2.4 | μM |

TABLE 2

| Target gene | Primer Name (SEQ ID) | Sequence (5'->3') |
|---|---|---|
| N gene | F3 (1) | GTCATTTTGCTGAATAAG CATAT |
| | B3 (2) | GAGTCAGCACTGCTCATG |
| | FIP (3) | TAAGGCTTGAGTTTCATC AGCCTT-ACGCATACAAA ACATTCCCA |
| | BIP (4) | CAGAGACAGAAGAAACAG CAAACT-GATTGTTGCAA TTGTTTGGAG |
| | LB (5) | GTGACTCTTCTTCCTGCT GCAGATT |

TABLE 3

| Fluor-Primer Name | Quencher Probe Name | Quencher Probe Sequence |
|---|---|---|
| FAM-BIP | qBIP-15nt | TTTCTTCTGTCT CTG-IBFQ (SEQ ID NO: 6) |

Other volumes, concentrations, compounds, combination, and amounts may be used as the LAMP reagents in different embodiments.

RT-Lamp Primers

The mgLAMP reagents include a set of RT-LAMP primers. The LAMP primers may include any set suitable for target microorganism. For example, for the SARS-CoV-2 genome, any of the 11 primer sets shown in Table 4 may be used. For the 11 sets of RT-LAMP primers in Table 4 targeting various regions in the SARS-CoV-2 genome, the relative performance may be compared using in-tube amplification of extracted SARS-CoV-2 RNA. Based on such comparison, primer set 3, 6, 10, and 11 of Table 4 may be shown to have the lowest LOD (limit of detection) at 93 copies per 20-μL reaction with no false positives observed in triplicates of NTCs. For these four primer sets, the amplification curves may be examined to compare their amplification efficiency. Based on the rise time, the order of amplification efficiency is observed to be primer set 10≈11>3>6. The most efficient primer sets were 10 and 11. Accordingly, in some embodiments, primer set 10, 11, or 3 was used.

TABLE 4

| No | Primer | Sequence (5' to 3') | Target gene |
|---|---|---|---|
| 1 | F3 | TGGACCCCAAAATCA GCG (SEQ ID NO: 7) | N gene |
| | B3 | GCCTTGTCCTCGAGG GAAT (SEQ ID NO: 8) | |
| | FIP | CCACTGCGTTCTCCA TTCTGGTAAATGCAC CCCGCATTACG (SEQ ID NO. 9) | |
| | BIP | CGCGATCAAAACAAC GTCGGCCCTTGCCAT GTTGAGTGAGA (SEQ ID NO: 10) | |
| | LF | TGAATCTGAGGGTCC ACCAA (SEQ ID NO: 11) | |
| | LB | TTACCCAATAATACT GCGTCTTGGT (SEQ ID NO: 12) | |
| 2 | F3 | CCAGAATGGAGAACG CAGTG (SEQ ID NO: 13) | N gene |
| | B3 | CCGTCACCACCACGA ATT (SEQ ID NO: 14) | |
| | FIP | AGCGGTGAACCAAGA CGCAGGGCGCGATCA AAACAACG (SEQ ID NO: 15) | |
| | BIP | AATTCCCTCGAGGAC AAGGCGAGCTCTTCG GTAGTAGCCAA (SEQ ID NO: 16) | |
| | LF | TTATTGGGTAAACCT TGGGGC (SEQ ID NO: 17) | |
| | LB | TAACACCAATAGCAG TCCAGATGA (SEQ ID NO: 18) | |
| 3 | F3 | TCCAGATGAGGATGA AGAAGA (SEQ ID NO: 19) | ORF1ab |
| | B3 | AGTCTGAACAACTGG TGTAAG (SEQ ID NO: 20) | |

TABLE 4-continued

| No | Primer | Sequence (5' to 3') | Target gene |
|----|--------|---------------------|-------------|
| | FIP | AGAGCAGCAGAAGTG GCACAGGTGATTGTG AAGAAGAAGAG (SEQ ID NO: 21) | |
| | BIP | TCAACCTGAAGAAGA GCAAGAACTGATTGT CCTCACTGCC (SEQ ID NO: 22) | |
| | LF | CTCATATTGAGTTGA TGGCTCA (SEQ ID NO: 23) | |
| | LB | ACAAACTGTTGGTCA ACAAGAC (SEQ ID NO: 24) | |
| 4 | F3 | CTGCACCTCATGGTC ATGTT (SEQ ID NO: 25) | ORF1a |
| | B3 | AGCTCGTCGCCTAAG TCAA (SEQ ID NO: 26) | |
| | FIP | GAGGGACAAGGACAC CAAGTGTATGGTTGA GCTGGTAGCAGA (SEQ ID NO: 27) | |
| | BIP | CCAGTGGCTTACCGC AAGGTTTTAGATCGG CGCCGTAAC (SEQ ID NO: 28) | |
| | LF | CCGTACTGAATGCCT TCGAGT (SEQ ID NO: 29) | |
| | LB | TTCGTAAGAACGGTA ATAAAGGAGC (SEQ ID NO: 30) | |
| 5 | F3 | TCATCAAACGTTCGG ATGCT (SEQ ID NO: 31) | |
| | B3 | TATGGCCACCAGCTC CTT (SEQ ID NO: 32) | |
| | FIP | CGACCGTACTGAATG CCTTCGAGAACTGCA CCTCATGGTCAT (SEQ ID NO: 33) | |
| | BIP | AGACACTTGGTGTCC TTGTCCCAGAAGAAC CTTGCGGTAAGC (SEQ ID NO: 34) | |
| | LF | CTGCTACCAGCTCAA CCATAAC (SEQ ID NO: 35) | |
| | LB | TCATGTGGGCGAAAT ACCAGT (SEQ ID NO: 36) | |
| 6 | F3 | CTGCACCTCATGGTC ATGTT (SEQ ID NO: 37) | |

TABLE 4-continued

| No | Primer | Sequence (5' to 3') | Target gene |
|----|--------|---------------------|-------------|
| | B3 | GATCAGTGCCAAGCT CGTC (SEQ ID NO: 38) | |
| | FIP | GAGGGACAAGGACAC CAAGTGTGGTAGCAG AACTCGAAGGC (SEQ ID NO: 39) | |
| | BIP | CCAGTGGCTTACCGC AAGGTTTTAGATCGG CGCCGTAAC (SEQ ID NO: 40) | |
| | LF | ACCACTACGACCGTA CTGAAT (SEQ ID NO: 41) | |
| | LB | TTCGTAAGAACGGTA ATAAAGGAGC (SEQ ID NO: 42) | |
| 7 | F3 | TGGCTACTACCGAAG AGCT (SEQ ID NO: 43) | N gene |
| | B3 | TGCAGCATTGTTAGC AGGAT (SEQ ID NO: 44) | |
| | FIP | TCTGGCCCAGTTCCT AGGTAGTCCAGACGA ATTCGTGGTGG (SEQ ID NO: 45) | |
| | BIP | AGACGGCATCATATG GGTTGCACGGGTGCC AATGTGATCT (SEQ ID NO: 46) | |
| | LF | GGACTGAGATCTTTC ATTTTACCGT (SEQ ID NO: 47) | |
| | LB | ACTGAGGGAGCCTTG AATACA (SEQ ID NO: 48) | |
| | F3 | ACCGAAGAGCTACCA GACG (SEQ ID NO: 49) | |
| | B3 | TGCAGCATTGTTAGC AGGAT (SEQ ID NO: 50) | |
| 8 | FIP | TCTGGCCCAGTTCCT AGGTAGTTCGTGGTG GTGACGGTAA (SEQ ID NO: 51) | |
| | BIP | AGACGGCATCATATG GGTTGCACGGGTGCC AATGTGATCT (SEQ ID NO: 52) | |
| | LF | CCATCTTGGACTGAG ATCTTTCATT (SEQ ID NO: 53) | |
| | LB | ACTGAGGGAGCCTTG AATACA (SEQ ID NO: 54) | |

TABLE 4-continued

| No | Primer | Sequence (5' to 3') | Target gene |
|----|--------|---------------------|-------------|
| | F3 | TGCTTCAGTCAGCTG ATG (SEQ ID NO: 55) | |
| | B3 | TTAAATTGTCATCTT CGTCCTT (SEQ ID NO: 56) | |
| 9 | FIP | TCAGTACTAGTGCCT GTGCCCACAATCGTT TTTAAACGGGT (SEQ ID NO: 57) | ORF1ab |
| | BIP | TCGTATACAGGGCTT TTGACATCTATCTTG GAAGCGACAACAA (SEQ ID NO: 58) | |
| | LF | CTGCACTTACACCGC AA (SEQ ID NO: 59) | |
| | LB | GTAGCTGGTTTTGCT AAATTCC (SEQ ID NO: 60) | |
| | F3 | GTTCCTCATCACGTA GTCG (SEQ ID NO: 61) | N gene |
| | B3 | GTTTGGCCTTGTTGT TGTT (SEQ ID NO: 62) | |
| 10 | FIP | GCCAGCCATTCTAGC AGGAGCAACAGTTAA GAAATTCAACTCC (SEQ ID NO: 63) | |
| | BIP | GATGCTGCTCTTGCT TTGCTACCAGACATT TTGCTCTCAA (SEQ ID NO: 64) | |
| | LB | GCTGCTTGACAGATT GAACCAG (SEQ ID NO: 65) | |

TABLE 4-continued

| No | Primer | Sequence (5' to 3') | Target gene |
|----|--------|---------------------|-------------|
| | F3 | GTCATTTTGCTGAAT AAGCATAT (SEQ ID NO: 66) | |
| | B3 | GAGTCAGCACTGCTC ATG (SEQ ID NO: 67) | |
| 11 | FIP | TAAGGCTTGAGTTTC ATCAGCCTTACGCAT ACAAAACATTCC CA (SEQ ID NO: 68) | |
| | BIP | CAGAGACAGAAGAAA CAGCAAACTGATTGT TGCAATTGTTTGGAG (SEQ ID NO: 69) | |
| | LB | GTGACTCTTCTTCCT GCTGCAGATT (SEQ ID NO: 70) | |

The performances of the 11 sets of RT-LAMP primers of Table 4 targeting various regions in SARS-CoV-2 genome was evaluated. These primers were compared using in-tube RT-LAMP assays of extracted ZeptoMetrix SARS-CoV-2 RNA. The sequences are tabulated in Table 4. All primer oligos were ordered from Integrated DNA Technologies (IDT, Coralville, IA) and resuspended in nuclease-free water (Thermo Scientific, Waltham, MA) as 100 μM stock solutions. Primer oligos of each set were combined in nuclease-free water to make 10× primer mix for a final concentration of 1.6 μM FIB and BIP, 0.2 μM F3 and B3, 0.8 μM LF and/or LB. RT-LAMP assays were set up as described by Warm-Start® LAMP Kit (DNA & RNA) (E1700, New England Biolabs, NEB, Ipswich, MA) and run in a qPCR platform (6300 Realplex4, Eppendorf, Hamburg, Germany) in the FAM channel. The assay recipe and temperature protocols are specified in Table 5. Extracted ZeptoMetrix SARS-CoV-2 RNA was spiked at 186, 93, 18.6, and 9.3 copies per reaction. Samples and NTCs for each primer set were tested in triplicates.

TABLE 5

| Test | Assay recipe | Varying component | Temperature protocol |
|------|--------------|-------------------|----------------------|
| a | Each 20-μL reaction contained 2 μL of template RNA for samples or nuclease-free water for no-template controls (NTCs), 10 μL of 2× WarmStart LAMP Master Mix, 0.4 μL of 50× LAMP Fluorescent Dye, 2 μL of 10× primer mix, and 5.6 μL of nuclease-free water. | Primer mix identity | 40 cycles of 65° C. for 1 min followed by 10 min of 80° C. heat inactivation in qPCR platform. |
| b | Each 20-μL reaction contained 10 μL of 2× WarmStart LAMP Master Mix, 0.4 μL of 50× LAMP Fluorescent Dye, 2 μL of 10× primer mix, 1 μL of 20 U/μL SUPERase•In ™ RNase Inhibitor (Invitrogen, Carlsbad, CA), 2 μL of sample or water, and complementary amount of nuclease-free water. | Concentration of Triton ™ X-100 (0.3%, 0.5%, and 0.7%) or Triton ™ X-405R (0.5%). | 60 cycles of 63° C. for 1 min followed by 10 min of 80° C. heat inactivation in qPCR platform. |

TABLE 5-continued

| Test | Assay recipe | Varying component | Temperature protocol |
|------|--------------|-------------------|---------------------|
| c | Each 20-µL reaction contained 10 µL of 2× WarmStart LAMP Master Mix, 0.4 µL of 50× LAMP Fluorescent Dye, 2 µL of 10× primer mix, 2 µL of sample or water, and complementary amount of nuclease-free water. | Concentration of Triton ™ X-100 or Triton ™ X-405R. | 60 cycles of 65° C. for 1 min followed by 10 min of 80° C. heat inactivation in qPCR platform. |
| d | Each 20-µL reaction contained 10 µL of 2× WarmStart LAMP Master Mix, 2 µL of 10× primer mix, 1.2 µL of 5M Betaine (PCR reagent, Sigma Aldrich, St. Louis, MO), 2 µL of sample or water, and complementary amount of nuclease-free water. | Quenching probe identity and concentration (1.6 µM, 2.4 µM, and 3.2 µM) | 65° C. for 40 min, heat inactivation at 80° C. for 10 min, and cooling at 20° C. for 2 min in qPCR platform. |

Table 5 shows the assay recipes and temperature protocols summarized for (a) primer screening, (b) in-assay viral lysis using primer set 3 of Table 4, (c) in-assay viral lysis using primer set 11 of Table 4, and (d) quenching probe selection and optimization.

QUASR-Based Fluorescence Detection

The specificity and fluorescence contrast RT-LAMP may be enhanced using quenching probes. To prevent false-positive results caused by non-specific primer hybridization that have been previously reported for LAMP, we designed and tested primer-specific probes that utilize the interactions between a dye-labelled primer and the complementary oligonucleotides as quenching probes for quenching of unincorporated amplification signal reporters (QUASR), a fluoro-primer and primer-quencher duplex. For QUASR-based fluorescence detection, one of the LAMP primers that forms a loop with its own amplification product, which can be FIP, BIP, LB, and LF, is fluorescently labelled at the 5'-end (FluoroP). To quench the unamplified FluoroP, a quenching probe with complementary oligonucleotides to FluoroP is labeled at 3'-end by a dark quencher molecule. Upon extension of FluoroP when the target is present in the sample, a thermodynamically favorable self-binding of this primer allows for the release of the quenching probe, thus emitting fluorescence signals. For FIP and BIP of primer set 11, probes with 7 to 17 nt were screened based on the $T_m$ and $\Delta G_{25° C.}$ values of probe-primer hybrid, primer-product hybrid, as well as interference of the quenching probe with other primers. The results indicate that the probes of varying lengths generally have low interference with other primers in reaction ($T_m$<10° C.) and under room temperature ($\Delta G_{25° C.}$>−5 kcal·mol$^{-1}$). These probes also have limited self-dimer formation. However, due to the low GC-content at the first 10 nt of 5'-ends of FIP and BIP at 40% and 50%, respectively, the probes should have lengths >9 nt to achieve a probe-primer $T_m$>40° C.

The fluorescence contrast and interference to amplification of the QUASR quenching probes were then experimentally studied for qFIP12nt, qFIP17nt, qBIP10nt, and qBIP15nt using extracted RNA in regular in-tube RT-LAMP. The probe-FluoroP $T_m$ values for these four designs span from 43.2 to 61.6° C. Images of NTCs and target-spiked samples for 1.6, 2.4, and 3.2 µM of the quenching probes are shown in FIG. 11, with fluorescence intensity measurements and signal-to-noise ratio (S/N).

Figure 11:
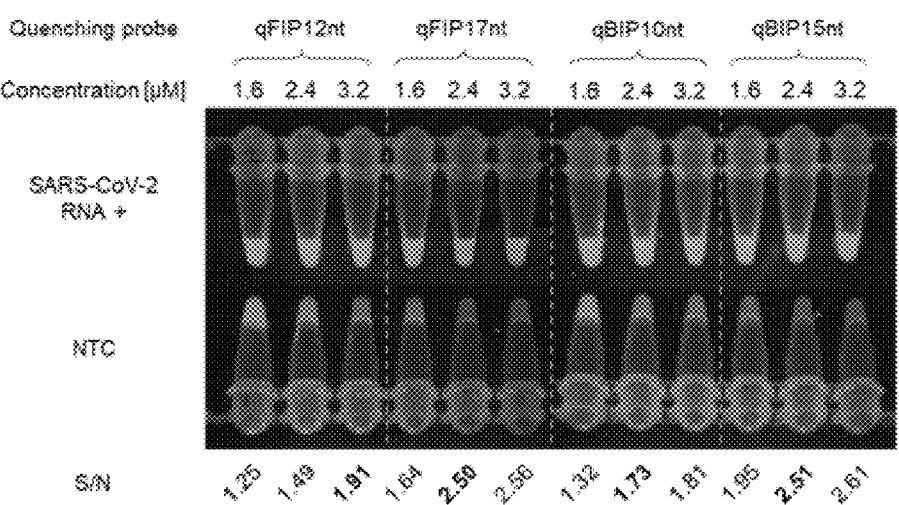
FIG. 11 are example photos of the RT-LAMP reactions using QUASR taken by a smartphone under the E-gel imager.

FIG. 11 are example photos of the RT-LAMP reactions using QUASR taken by a smartphone under the E-gel imager. Four quenching probes (qFIP12nt, qFIP17nt, qBIP10nt, and qBIP15nt) were tested at concentrations of 1.6, 2.4, and 3.2 µM. The upper row tubes contained extracted SARS-CoV-2 RNA spiked at 384 copies per reaction. The lower row shows corresponding no template controls (NTCs). S/N values were calculated based on the ratio of fluorescence intensity of target-spiked samples and NTCs.

Generally, extending the probe length for each FluoroP or increasing the concentration of each probe resulted in lower background fluorescence in NTC without noticeably reducing the fluorescence intensity of the positive samples except for qFIP17nt. For each quenching probe, sufficient S/N was achieved with 3.2 µM qFIP12nt, 2.4 µM qFIP17nt, 2.4 µM qBIP10nt, and 2.4 µM qBIP15nt. Using the concentrations above, the LODs of assays using the 4 QUASR designs were tested with extracted RNA. The lowest LOD at 192 copies per reaction was achieved with both qFIP12nt and qBIP15nt. For qFIP17nt, the probe-primer hybridization has the highest $T_m$ at 61.6° C., which implicates a considerable extent of primer binding at the RT-LAMP temperature of 65° C. and thus hindered amplification. The results indicate that the quencher would be non-inhibitory when the probe-primer $T_m$ falls below 5° C. lower than the reaction temperature. For qBIP10nt, stochasticity might have been accountable for the higher LOD observed. Therefore, based on its optimal quenching of background fluorescence, highest S/N, and lowest LOD, 2.4 µM qBIP15nt was selected for some embodiments of the mgLAMP methods and systems. Before the QUASR probing strategy was selected, performances of QUASR and another target-specific probe named molecular beacon was also investigated and compared.

QUASR quenching probes for primer set 11 with 7 to 17 nucleotides (nt) complementary to the 5'-ends of the FIP and BIP were studied. DINAMelt web server was used to calculate secondary structure formation and $\Delta G_{25° C.}$ and melting temperature ($T_m$) of probes versus each primer. Fluorophore-labelled FIP and BIP primers (5'FAM-FIP and 5'FAM-BIP) and four 3' Iowa Black® FQ (IBFQ)-labelled quenching probes were obtained from IDT. The quenching probes include qFIP12nt (5'-TTTCTTCTGTCTCTG-3'IBFQ (SEQ ID NO:71)), qFIP17nt (5f-ATGAAACT-CAAGCCTTA-3'IBFQ (SEQ ID NO:72)), qBIP10nt (5'-TCTGTCTCTG-3'IBFQ (SEQ ID NO:73)), and qBIP15nt (5f-TTTCTTCTGTCTCTG-3'IBFQ (SEQ ID NO:74)). To prepare the 10× primer mix when using quenching probes, regular non-labelled FIP or BIP was replaced by the corresponding 5'FAM-FIP or 5' FAM-BIP at the same concentration of 1.6 µM. Each quenching probe was tested at concentrations of 1.6 μM, 2.4 μM, and 3.2 μM (recipe and temperature protocol in Table 5, row d). Extracted ATCC SARS-CoV-2 RNA was spiked at 384, 192, and 96 copies per reaction. After RT-LAMP reaction, the tubes were illuminated by an E-gel Safe imager (Invitrogen, Carlsbad, CA) and imaged using a Google Pixel 4 (Google, Mountain View, CA) smartphone camera with night mode, as shown in FIG. 11. To avoid ambient light interference, the images were processed (MATLAB R2017b, MathWorks, Natick, MA) to force zeros in the red channel and measure the fluorescence intensity in the green channel using the interactive 'impixelinfo' function. Three random points were measured in each tube.

Microorganism Lysis

Effective viral lysis is desirable for robust NAA-based detection. To seamlessly connect membrane filtration and downstream RT-LAMP assays on the membrane, an extraction-free workflow is useful. SARS-CoV-2 has 30-kb of single-stranded RNA packed in a lipid envelope with membrane proteins and enveloped proteins embedded. As alternatives to commercial kit-based SARS-CoV-2 RNA extraction and purification, simplified methods are disclosed herein, non-ionic detergents, including as Triton™ X-100, X-405R, and Tween® 20, may be used to extract viral RNA by pre-assay incubation. They are generally well-tolerated in PCR or LAMP assays. Therefore, a non-ionic detergent can be used to lyse viral particles in-assay during the disclosed RT-LAMP.

The in-assay viral lysis performance of Triton™ X-100 and Triton™ X-405R was determined by comparing Triton-added RT-LAMP assays using directly spiked inactivated SARS-CoV-2 particles to Triton-free assays spiked with extracted RNA. RT-LAMP reactions were monitored with real-time fluorescence emitted by a DNA-intercalating LAMP dye, and the amplification curves recorded. All the target-spiked samples, either viral particles or extracted RNA, contained targets at a well-above-LOD concentration of 186 copies per reaction. Without a detergent additive, directly spiked SARS-CoV-2 particles went undetected in all samples, whereas samples spiked with extracted RNA had a consistent time-to-threshold of 23.11±0.32 minutes.

Across all tested conditions, 0.5% Triton™ X-100 was observed to be most suitable with a comparably short and consistent time-to-threshold of 22.35±1.58 minutes. This result indicates that the spiked Covid-19 viral particles were successfully lysed by 0.5% Triton™ X-100 in the assay to release their RNA templates for amplification. It was also observed that for Triton™ X-100, increasing concentrations led to reduced slopes of the exponential amplification phase. The deceleration of amplification was likely due to the inhibition effect of high non-ionic detergent concentration on the DNA polymerase activity. The effect of a non-ionic detergent additive to RT-LAMP may vary for individual primer sets. In similar in-assay viral lysis experiments conducted using another primer set (number 11), non-specific amplifications were observed for NTCs of all Triton™ X-100 concentrations, which could be resolved by designing product-specific probes such as QUASR or molecular beacons. The observed difference in the effect of Triton™ X-100 on different primer sets could be due to the distinctive configuration of each target region, since non-ionic detergents were reported to enhance PCR amplification by stabilizing DNA polymerase and preventing formation of secondary structures.

For an extraction-free RT-LAMP assay, the viral lysis performance of Triton™ X-100 (t-Octylphenoxypolyethoxyethanol) and Triton™ X-405 (Sigma Aldrich, St.

Louis, MO), as assay additives was evaluated using in-tube RT-LAMP on primer set 3. Both detergents were prepared as 10% stock by dilution in water. RT-LAMP assays were tested with 0.3%, 0.5%, and 0.7% Triton™ X-100 and 0.5% Triton™ X-405R (recipe and temperature protocol as listed in Table 5, row b). Zeptometrix SARS-CoV-2 particles were spiked at 186 copies per reaction. As a comparison, no-Triton controls were included with the same spiking concentration of extracted RNA and SARS-CoV-2 particles from Zeptometrix. Samples and NTCs for each tested detergent concentration and no-detergent controls were tested in triplicates. Similar tests were conducted for primer set 11 with Zeptometrix SARS-CoV-2 particles spiked at 186, 93, 18.6, and 9.3 copies per reaction (recipe and temperature protocol in Table 5, row c).

Overall, without any sample pretreatment or reagent removal required, the disclosed extraction-free RT-LAMP assay using 0.5% Triton™ X-100 was able to lyse the Covid-19 viral particles during the RT-LAMP reaction with no noticeable delay in amplification.

Sealing on Glass Slide and Incubation

On a glass slide with a Frame-Seal incubation chamber 118, a mixture of PEG hydrogel monomers and RT-LAMP reagents is added on top of the virus-loaded membrane 108. After filtration, the PCTE membrane may be dried at room temperature and then placed on a 75 mm×25 mm VWR VistaVision™ Microscope Slide (VWR International, Radnor, PA) using 1 μL of 50% PBS buffer (Corning, Corning, NY) and 50% Glycerol (Sigma-Aldrich, St. Louis, MO) mixture. A Frame-Seal™ in situ PCR and Hybridization Slide Chamber (9×9 mm; Bio-Rad, Hercules, CA) may be placed onto the membrane 108 as a vessel for further mgLAMP assay. Other slides and chambers may be used in some embodiments.

Next, the prepared slide is sealed and heated for incubation 122. The above mgLAMP reaction mix may be immediately loaded into the chamber 118 and then covered with a transparent film 120 (ThermalSeal® RT™ Sealing Film, Genesee Scientific, San Diego, CA). After covering, the mgLAMP mixture is allowed to gel at room temperature for 5 minutes, allowing the hydrogel to crosslink, and then incubated in a PCR machine (MJ Research PTC-100, Watertown, MA) at 65° C. for 30 minutes. The loaded slide 117 may be subjected to 30 minutes of RT-LAMP reaction in an mgLAMP PID 124, for example, one of the PIDs 200, 300 disclosed herein.

The hydrogel concentration and incubation times may be any suitable values depending on the application. In some embodiments, the hydrogel concentration of the mgLAMP mixture may vary, e.g., the gel concentration may be any value between 2.5% and 10% (w/v), for example, 5%, 7.5%, and 10% (w/v) and incubation time may be any value between 20 minutes and 60 minutes, e.g., 30 minutes and 40 minutes, depending on the application.

On top of the virus-loaded membrane, the PEG hydrogel containing RT-LAMP reagents may be formed via the thiol-Michael addition reaction between 4-arm PEG-acrylate and PEG-dithiol. The nano-porous hydrogel structure allows for the diffusion of small molecules, such as DNA polymerase and primers, while confining larger-sized viral particles, nucleic acid templates, and amplification products to facilitate formation of bright dots for fluorescence counting.

To achieve an appropriate RT-LAMP reaction efficiency in the mgLAMP system, gel concentrations that were varied from 2.5%, 5%, 7.5%, and 10% (w/v) were tested. Larger amplicon dots were observed with decreasing gel concentration, which theoretically leads to larger mesh size and thus increased diffusivity. In 5% and 7.5% (w/v) gel, the sizes and boundaries of formed amplicon dots were discernible and clear in smartphone images. With 10% (w/v) gel, the fluorescent amplification products appeared to be highly localized by the hydrogel network, forming faint and small amplicon dots hardly visible using the smartphone. At 2.5% (w/v) gel concentration, the amplicon dots became difficult to count as the boundaries between amplicon dots were barely formed. Other than expanding the dot size, reducing gel concentration from 10% to 5% also boosted the dot count from 80±26 to 201±21, which could be explained by higher amplification efficiency with a loosened hydrogel network leading to increased diffusivity of amplification intermediate structures and amplification products. Therefore, a gel concentration of 5% may be used. At this gel concentration, the incubation time may be 30 minutes.

Fluorescent Amplicon Dot Counting

After incubation is completed, the results of the mgLAMP reaction are quantified 125. With the fluorescence illumination in the PID 124, fluorescent signals emitted from the loaded, incubated slide 126 can be imaged using a smartphone or other handheld device and counted by a cloud server 128 running a machine learning-based image processing program to deliver absolute quantification to the user.

To facility the POU applicability of the mgLAMP methods and systems, an image processing application program is provided for recognizing fluorescent amplicon dots in one or more pictures of the loaded, incubated slide, taken by a smartphone through the viewing port of the PID 124 while the illumination is turned on. Quantitative mgLAMP reaction results are generated by counting amplification dots.

Smartphone imaging of the fluorescence amplification dots may be robust enough to deliver comparable image quality for dot counting. For example, the endpoint fluorescence image of mgLAMP incubation chamber 118 may be illuminated by the E-gel Safe imager and captured using a Google Pixel 4 smartphone camera using the night mode. Paired with smartphone imaging, the image processing computer program can be used for point-of-sample-collection quantitative result determination.

Figure 12:
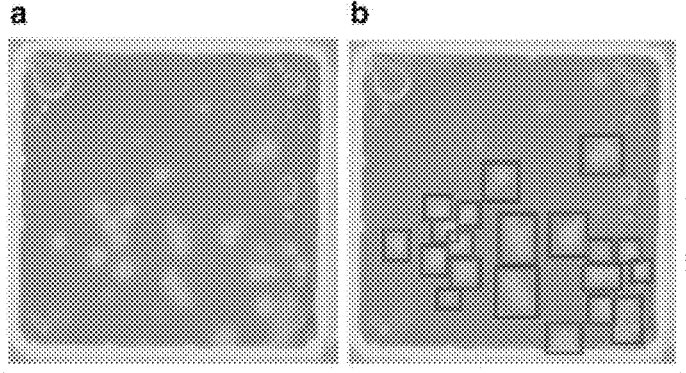
FIGS. 12A-B show an example photo of a finished mgLAMP slide taken by a smartphone and analyzed by a machine learning program, illuminated by a fluorescent light source.
Figure 13:
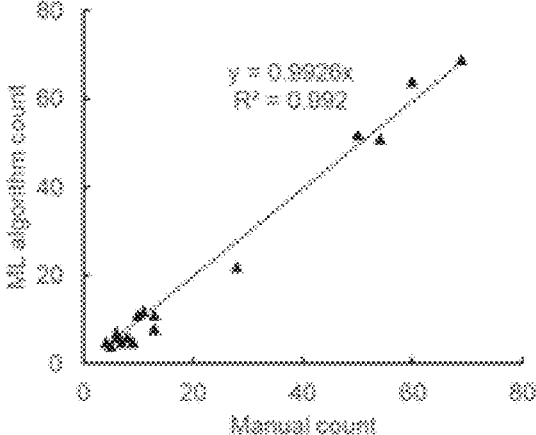
FIG. 13 shows a graph comparing auto-counted amplicons in slide images with an amplicon manual count of the same images.

The image processing computer program can use a machine learning model to identify mgLAMP amplicons. In some embodiments, the machine learning model may be trained for 27 node hours using AutoML Vision module of the Google Cloud Platform by feeding ten fluorescence microscope mgLAMP images with pre-labelled, manually identified amplicon dots. Models may be trained with any suitable number of training images with any suitable number of node hours training time. For example, up to 96 mgLAMP images and 20-54 node hours training time may be used. In some embodiments, the model may be trained with 16 mgLAMP slide images. An example of this approach is shown in FIGS. 12A-B. FIG. 12A shows an example photo of a finished mgLAMP slide taken by a smartphone, illuminated by a fluorescent light source. FIG. 12A shows the same image, where the squares highlight the recognized amplicon dots by the trained Google AutoML Vision model. The accuracy of the trained ML model in amplicon dot counting is compared with manual counting, as shown in the graph of FIG. 13. Sixteen smartphone images were tested, and the results were compared to manual counting of the same images. In FIG. 13, the dotted line represents the linear fitting of the observed ML counts versus manual counts, with the equation and R-square displayed. In the images shown in FIG. 12, 20 out of 24 signals were correctly recognized by AutoML vision with no false positive and 4 false negatives. For the 16 tested images, the results from the machine learning algorithm were close to those obtained by manual counting (y=0.9926x, $R^2$=0.992) (graph shown in FIG. 13). The deviations from manual counting were mostly false negatives due to the low fluorescence intensity of the dots or vague boundaries between the adjacent dots with occasional false positives.

For automated signal counting, the machine-learning model may use AutoML Vision module of the Google Cloud Platform (Google, Mountain View, CA), as mentioned above. To establish the model, ten fluorescence microscope images may be uploaded to Google Cloud Storage and all fluorescent amplicon signals in those images are first labelled manually. Each image with more than 50 amplicon signals may be split into a 3×3 grid (a total of 9 smaller images), and each of the smaller images may be uploaded and labelled separately to meet the Google Cloud Vision's limit of 50 signals per image. All images uploaded are categorized randomly as training, testing and validation images with an 8:1:1 ratio. Training of the machine learning model used the high accuracy goal setting and 27 node hours. The trained model was deployed on a network server for online access from an Internet enabled smartphone or other device.

In some embodiments, fluorescence microscopy may be used to identify and detect amplicon dots. Fluorescence images of the finished mgLAMP slide may be captured by a Leica DMi8 fluorescence microscope (Leica Microsystems, Wetzlar, Germany) to calibrate the counting of amplicon dots using ImageJ 1.52a software. For 3D imaging of a post-reaction mgLAMP slide, an inverted confocal fluorescence microscope (ZEISS LSM 980 with Airyscan 2, Zeiss, Oberkochen, Germany) may be used in the FAM channel with a 20× objective. The accompanied software (ZEN blue 3.3, Zeiss, Oberkochen, Germany) may be employed for z-stack image acquisition and 3D rendering.

Portable Integrated Devices (PIDs)

Figure 4:
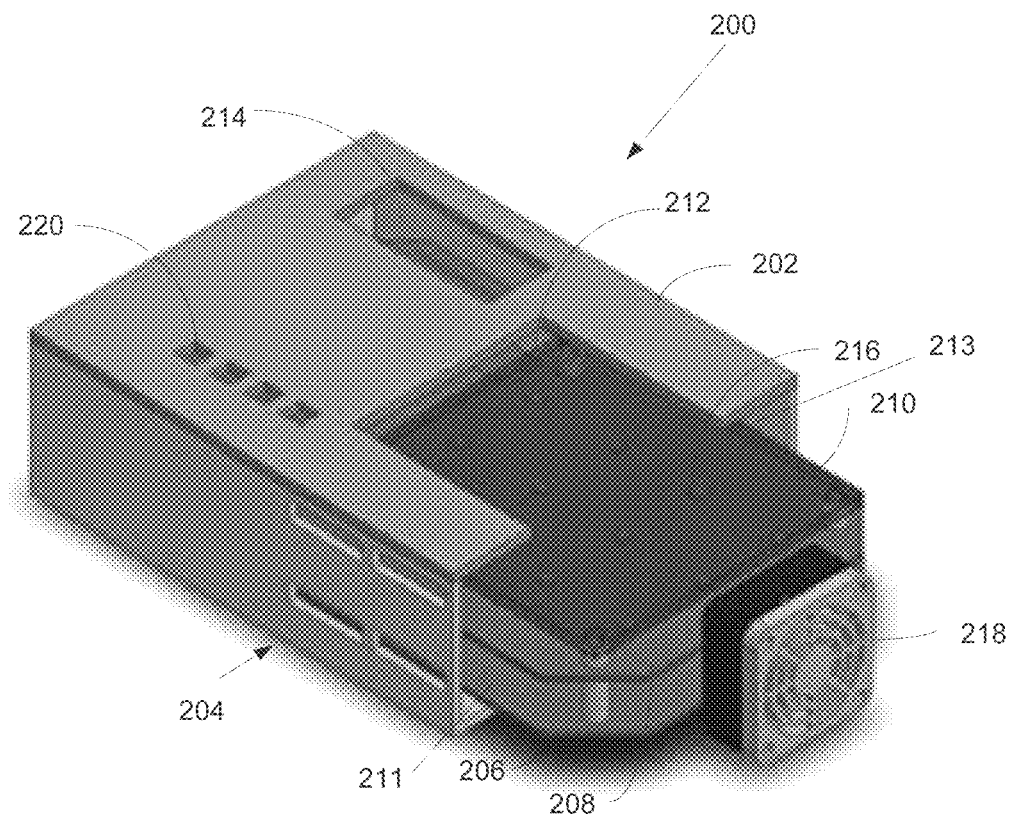
FIG. 4 is a partial cut-away perspective view of an exemplary portable integrated device usable with the mgLAMP methods and systems described herein.

FIG. 4 is a partial cut-away perspective view of an exemplary portable integrated device (PID) 200 usable with the mgLAMP methods 40, 100 and system 10 described herein. The PID 200 is a light weight device that integrates the incubation, illumination, fluorescence emission filtering, and viewing functions of the mgLAMP methods and systems. The PID 200 may be fabricated using plastic structures fabricated by 3D printing (Makerbot METHOD X, Makerbot, Brooklyn, NY) using PLA and ABS filaments (Makerbot, Brooklyn, NY) and commercially-available electrical components. In some embodiments, the PID 200 is configure to process nine mgLAMP reactions simultaneously through 30 minutes of RT-LAMP heating at 65° C., fluorescence excitation with high-powered LEDs, and fluorescence emission filtering. The compact, low-cost PID 200 can run assays without access to biological laboratories or the need for bulky lab-based equipment. The PID 200 may be battery powered and low voltage.

Figure 5:
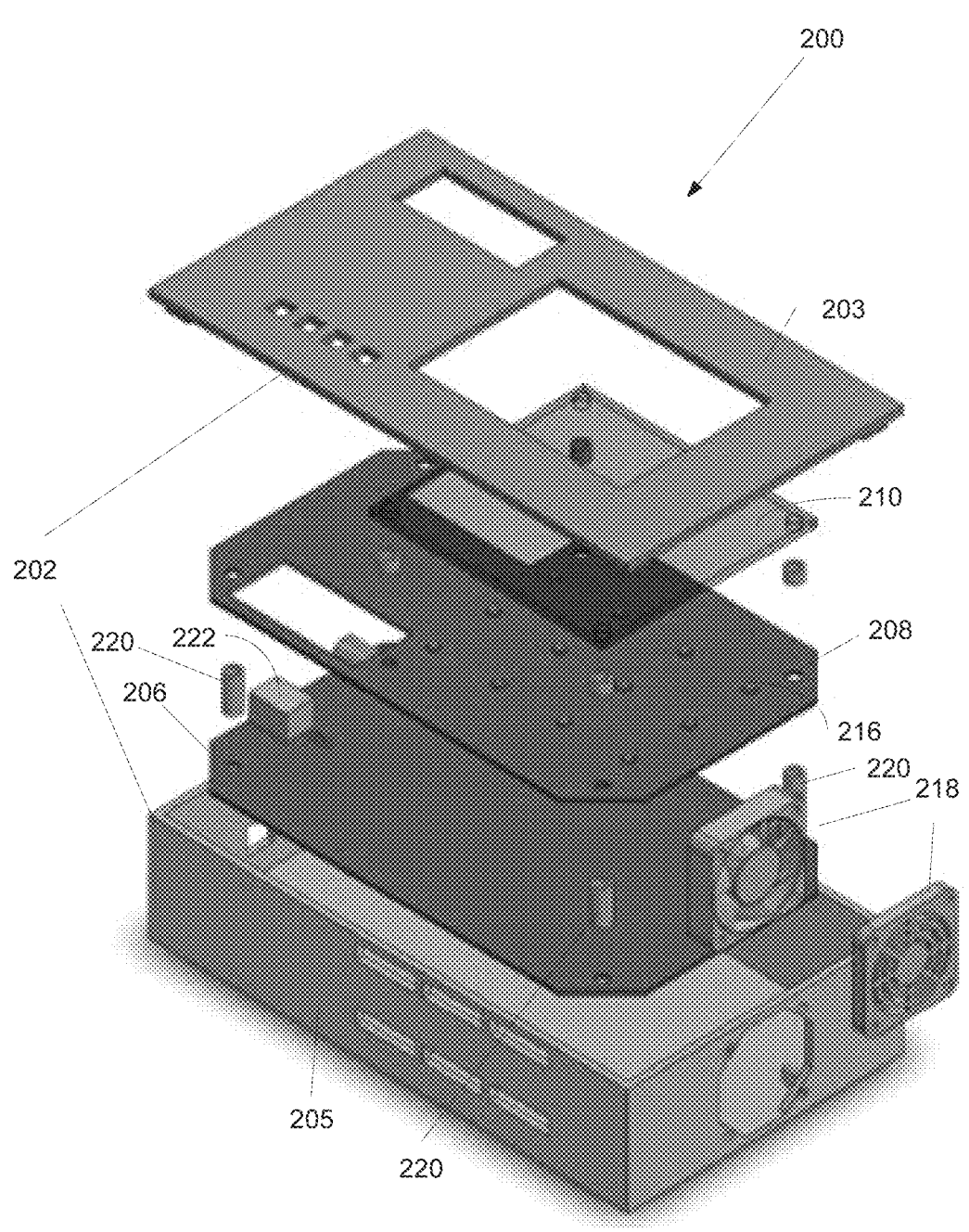
FIG. 5 is an exploded perspective view of the portable device of FIG. 4.

The PID 200 includes a plastic housing 200 having a lid 203 (FIG. 5) and box housing 205 (FIG. 5). Two rows of three slots 204 each are formed in one side of the box 205. The slots are for inserting loaded slides into the PID 200. The lid 203 includes viewing port opening 212, a display opening 214, and control button openings 220. The viewing port opening 212 permits a user to photograph or visually inspect the slides while inserting into the PID 200. The display opening 214 permits the user to see and LCD display, the button opening permit the user to access control switch to operate the PID 200.

Inside the housing 202 are located an incubation printed circuit board (PCB) 206 and an illumination PCB 208 having an array of blue and/or UV LEDs 216 mounted thereon. Plastic spacers 220 (FIG. 5) separate the PCBs 206, 208 (FIG. 5). The separation between the PCBs 206, 208 creates an incubation chamber 211, which can receive loaded slides through the lower row of slots 204.

The illumination PCB 208 and lid 203 form an upper illumination chamber 213 therebetween. The upper chamber 213 receives loaded, incubated slides through the upper row of slots 204.

An optical filter film 210 is placed over the LED array 216 to filter the light emitted from the LEDs 216. The optical filter may be a blue filter with a wavelength cutoff of about 480 nm.

A fan 218 is included to circulate air within the incubation chamber 211.

FIG. 5 is an exploded perspective view of the PID 200 of FIG. 4. FIG. 5 shows some of the electrical components 222 that may be mounted on the PCBs 206, 208.

Figure 6:
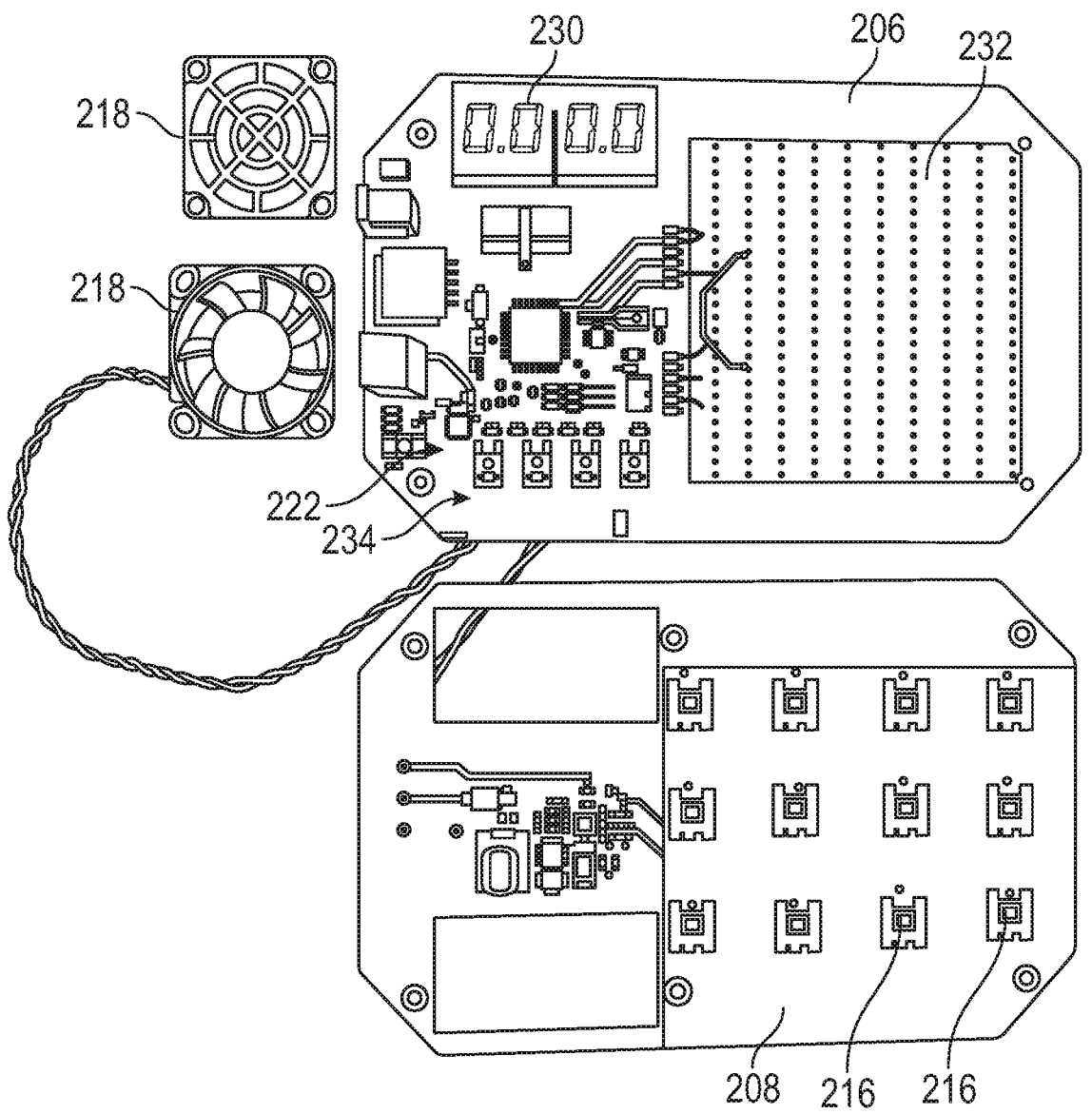
FIG. 6 is a top down view of some of the components included in the portable device of FIG. 4.

FIG. 6 is a top down view of some of the components included in the PID 200 of FIG. 4. The incubation PCB 206 includes and LCD display 230, heating element 232, control switches 234 and controller circuitry 222.

The controller circuitry 222 may be any suitable means for controlling the operation of the PID 200 and interfacing with the user controls 234. For example, the controller 222 may include one or more processors for executing instructions or code, such as one or more digital signal processors (DSPs), general purpose microprocessors, application specific integrated circuits (ASICs), field programmable logic arrays (FPGAs), or other equivalent integrated or discrete logic circuitry. The controller may also include memory. The memory and processor may be combined as a single chip.

The functions of the controller may be implemented in hardware, software, firmware, or any suitable combination thereof. If implemented in software, the functions may be stored as one or more instructions or code on a computer-readable medium (e.g., memory) and executed by a hardware-based processing unit (e.g., a processor). Computer-readable media may include any computer-readable storage media, including data storage media, which may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disc storage, magnetic disk storage, or other magnetic storage devices, flash memory, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

The LED array PCB includes driver circuitry for the LED array 216 and interconnects for electrical communication with the incubation PCB 206.

During operation, the incubation temperature and time may be programmed by the user using control switches 234. One or more incubation temperature and time cycles may be entered via the controls 234. For example, three consecutive steps (A, B, and C) can be programmed by using buttons 234 to navigate between each cycle setting and to decrease or increase the temperature and duration values. For example:

AT: temperature of step A (between 25° C.-70° C.)
BT: temperature of step B (between 25° C.-70° C.)
CT: temperature of step C (between 25° C.-70° C.)
A [ ]: duration of step A from 0 to 120 minutes.
B [ ]: duration of step B from 0 to 120 minutes.
C [ ]: duration of step C from 0 to 120 minutes.

If a single heating step is desired, BT and CT values may be set to "25" and duration for these steps to 0 minutes.

Once the incubation program is entered, the user can start the incubation by clicking one or the buttons 234 until display shows "off". Another button press may then start the incubation cycle(s). The display will show a predefined symbol while heating to reach the temperature selected for step A. The PID 200 then runs through the programmed cycles, switching from step A, to B, and finally to C.

To incubate slides with the PID 200, the following steps are followed, after the PID cycle(s) are programmed. Step 1: place the prepared slide(s) in one of the bottom slots 204 for incubation. Step 2: launch the incubation by following the "incubation cycle start" instructions (above). Step 3: once the incubation is finished, the slide(s) are carefully removed from the bottom slots and placed in the upper slots, respectively, for results reading via illumination. Step 4: press the LED illuminate button included in the switches 234. The high intensity LEDs will power on for a predetermined time, e.g., 10 seconds. Step 5: take a picture of the sample when the LEDs are powered and use the computer program provided to analyze the picture (vide infra).

Figure 7:
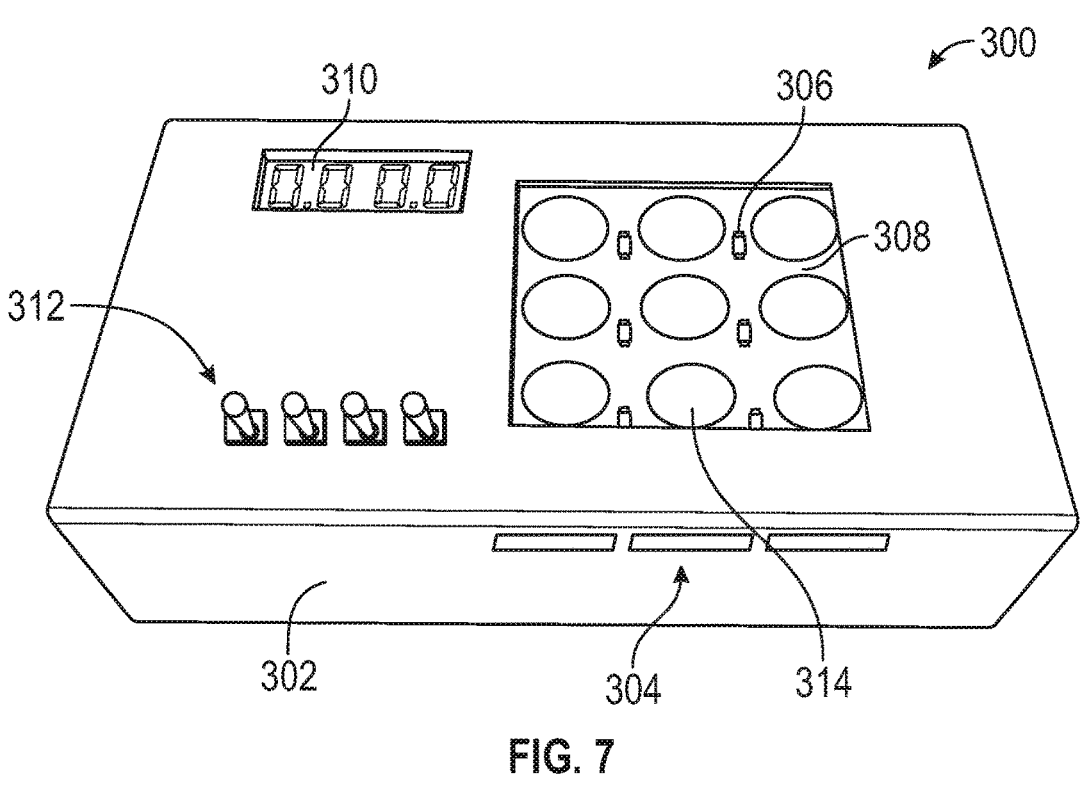
FIG. 7 is a top-down perspective view of another exemplary portable integrated device usable with the mgLAMP methods and systems described herein.

FIG. 7 is a top-down perspective view of another exemplary PID 300 usable with the mgLAMP methods 40, 100 and system 10 described herein. Like the PID 200 of FIGS. 4-6, the PID 300 of FIG. 7 is a light weight device that integrates the incubation, illumination, fluorescence emission filtering, and viewing functions of the mgLAMP methods and systems. The PID 300 may be fabricated using plastic structures fabricated by 3D printing (Makerbot METHOD X, Makerbot, Brooklyn, NY) using PLA and ABS filaments (Makerbot, Brooklyn, NY) and commercially-available electrical components. In some embodiments, the PID 300 is configure to process nine mgLAMP reactions simultaneously through 30 minutes of RT-LAMP heating at 65° C., fluorescence excitation with high-powered LEDs, and fluorescence emission filtering. The compact, low-cost PID 300 can run assays without access to biological laboratories or the need for bulky lab-based equipment. The PID 300 may be battery powered and low voltage. The PID 300 may also include controller circuitry that performs substantially similar functions as that of the control circuitry 222 included in PID 200 of FIG. 4.

The main difference between the PID 300 of FIG. 7 and the PID 200 of FIG. 4 is that the PID 300 has only one row of slide slots 304 for in the box housing 302 and a single, combined incubation-illumination internal chamber, instead of separate chambers, as described in connection with the PID 200 of FIG. 4.

The PID 300 includes a plastic housing 302 having openings similar to those described in connection with PID of FIGS. 4-6, except there is only one row of three slots 304. The PID 300 also includes an LED display 310, an LED array 306, a blue filter 308, and control switches 312. The PID 300 may also include a fan and incubation PCB (not shown) similar in function to those described in connection with PID 200. These components may have the same functions as described for PID 200 of FIG. 4.

Figure 8:
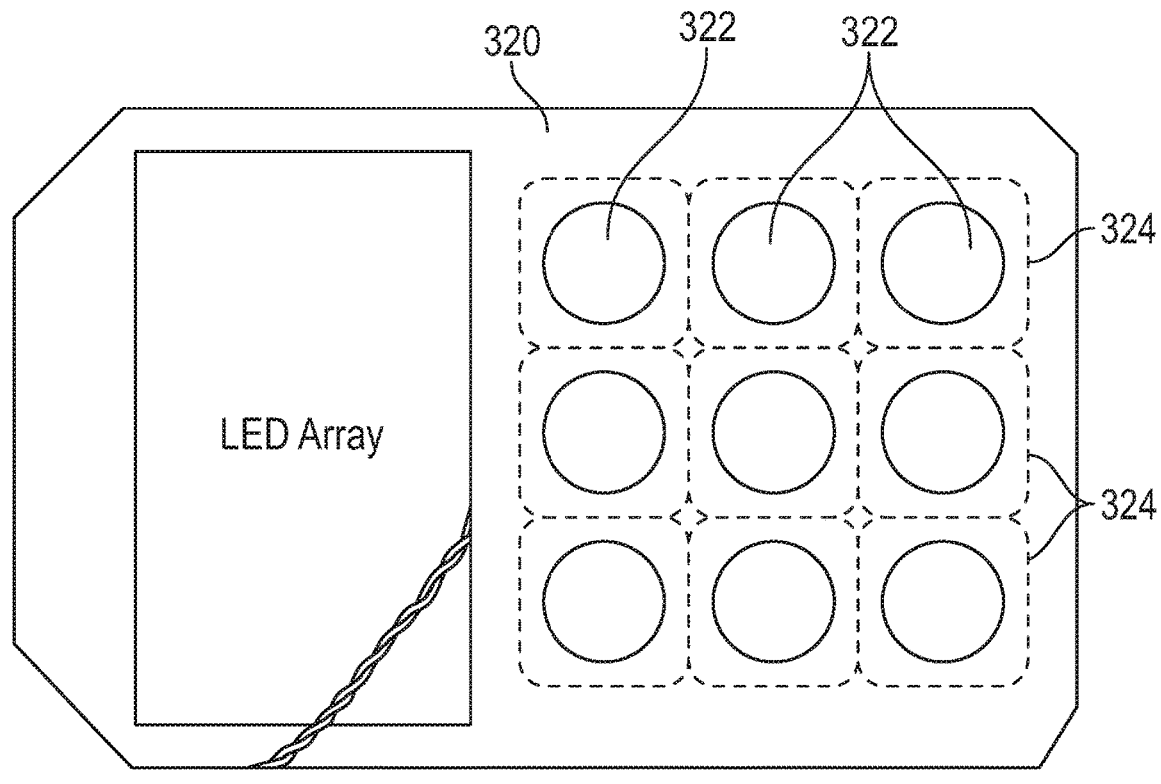
FIG. 8 is a top-down view of the LED array circuit board of the portable integrated device of FIG. 7.

FIG. 8 is a top-down view of the LED array PCB 320 of the PID 300 of FIG. 7. The LED array PCB 320 includes blue and/or UV LEDs 324 and viewing holes 322 formed therein.

Figure 9:
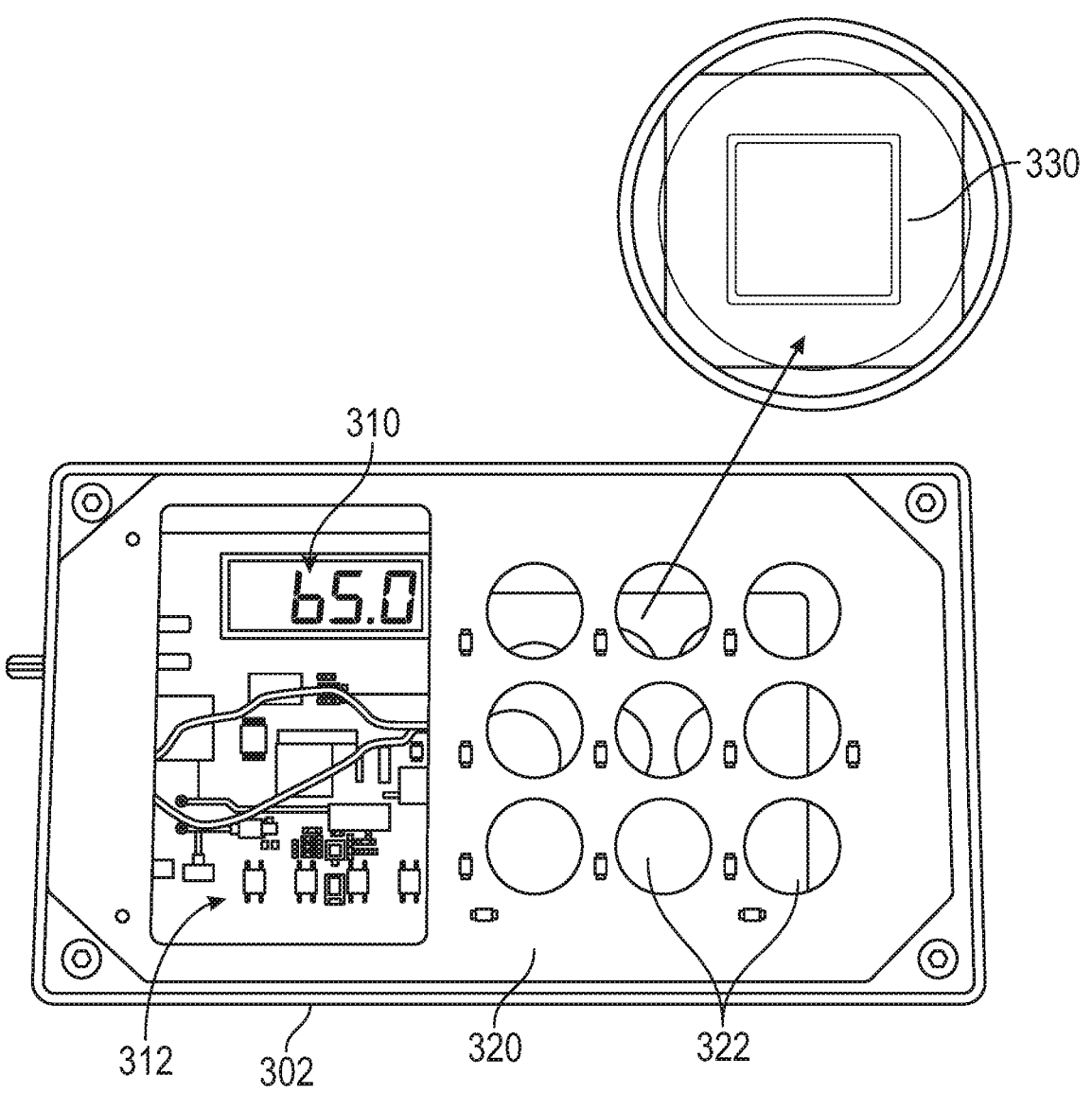
FIG. 9 is a top-down view of the portable integrated device of FIG. 7 with its lid removed and a detailed insert showing a loaded slide as viewed while it is in the portable device.

FIG. 9 is a top-down view of the PID 300 of FIG. 7 with its lid removed and a detailed insert showing a loaded slide as viewed while it is in the portable device 300. A user can visually inspect and photograph loaded slides 300 through the holes 322 form in the PCB 320, without having to move the slide from the lower to upper row of slots 304.

Figure 10:
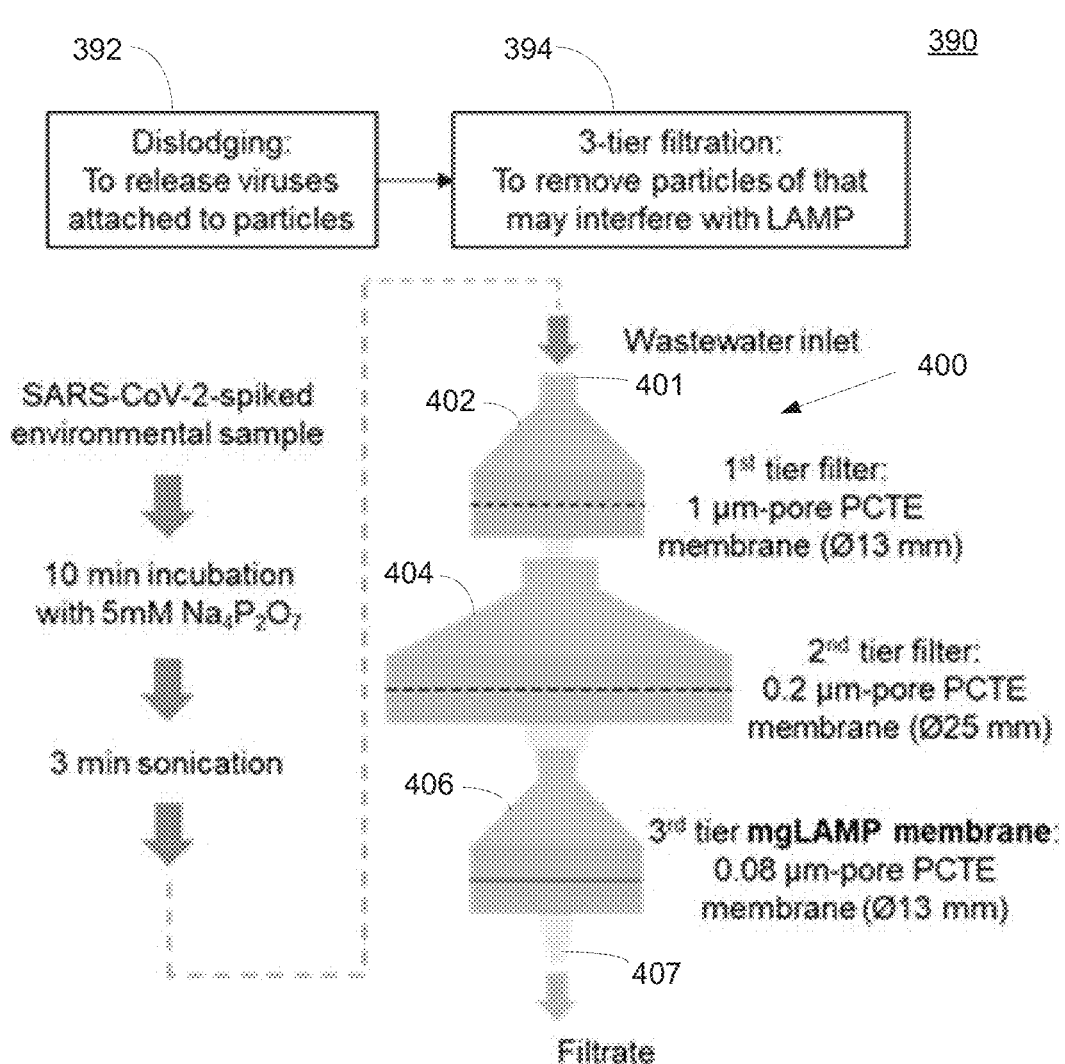
FIG. 10 is a schematic process diagram illustrating an exemplary pre-treatment process and filter system for pretreating mgLAMP samples.

FIG. 10 is a schematic process diagram 390 illustrating exemplary pretreatment process (steps 392, 394) and filter system 400 for pre-treating mgLAMP samples. The pretreatment process for environmental or wastewater samples includes a dislodging steps 392 and 3-tier filtration steps 394 of environmental water and wastewater samples.

The dislodging steps 392 may be performed to separate target microorganisms from other particles in the sample. In the example shown, a SARS-CoV-2 spiked sample is processed. The protocol for the virus dislodging step 392 involves incubating the sample in a sodium pyrophosphate decahydrate solution ($Na_4P_2O_7.10H_2O$, available from Sigma Aldrich, St. Louis, MO) prepared into a 100 mM stock by dissolving in Milli-Q water, and adding to a spiked environmental sample to a final concentration of 5 mM. The sample is then incubated at room temperature for 10 minutes. Next, the incubated sample is sonicated (using 46 kHz, 30 W, Bransonic™ Ultrasonic Cleaner Model B200, available from Branson Ultrasonics, Brookfield, CT) in an ice-bath for 3 minutes. During the 3 minutes of sonication, the samples may be taken out and gently shaken by hand for 30 seconds after every minute of sonication.

After the virus dislodging pretreatment steps 392, the samples are loaded into a 5-mL syringe for multi-tier filtration (step 394). Step 394 may use primary filter 400 (which include first tier 402 and optional second tier 404 filters) for removing larger particles from the sample and filter membrane 406 for removing smaller particles. The 3-tier filter includes an inlet 401 for admitting the sample and an outlet 407 for passing the filtrated sample.

For the 1st tier of filtration, a 13 mm PCTE membrane with 1 µm pores may be used. The 2nd tier filter may employ a 25 mm PCTE membrane with 0.2 µm pores. Other pores sizes may be used, and in some embodiments the $2^{nd}$ tier filtration is omitted. The filtration membranes are not supported by any mesh spacer for the first two tiers. The 3rd tier filter 406 may contain a 13 mm 0.08 µm-pore PCTE membrane supported by a 13 mm PETE drain disc mesh spacer. The membranes may be loaded into 13 mm or 25 mm Swinnex filter holders (available from MilliporeSigma, Burlington, MA), respectively. The filter holders may be connected and attached to the LuerLock of the syringe. A syringe pump can be used to drive the sample flowing through the 3-tier filtration at a flow rate of about 0.5 mL/min. The membrane from the 3rd tier can be retrieved for mgLAMP analysis using the system and methods described herein. In some embodiment, the 2nd tier of filtration may be omitted.

Figure 15:
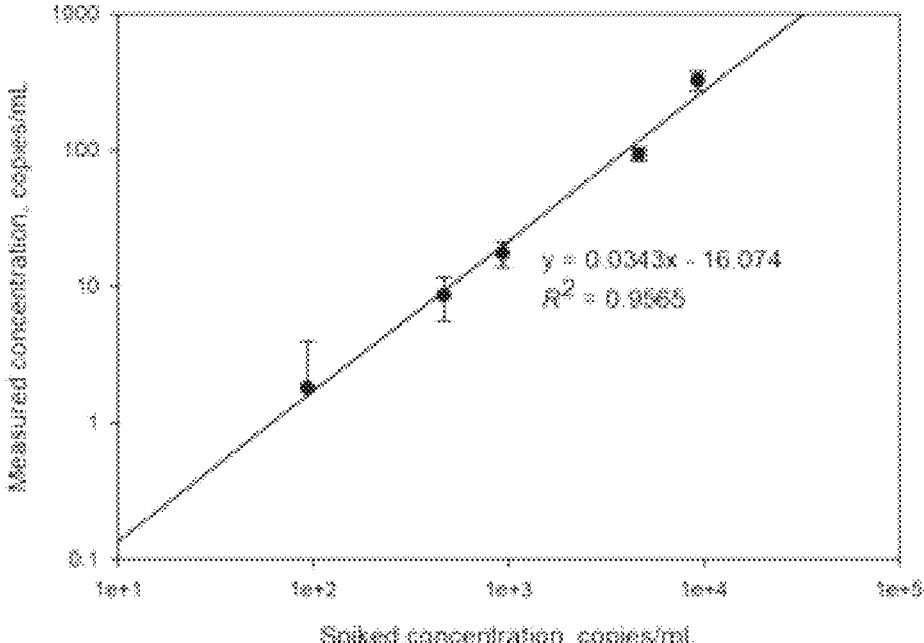
FIG. 15 shows a graph comparing measured SARS-CoV-2 concentration to the spiked SARS-CoV-2 concentration in surface water experimental testing.

FIG. 15 shows a graph comparing measured SARS-CoV-2 concentration to the spiked SARS-CoV-2 concentration in surface water experimental testing.

Figure 14:
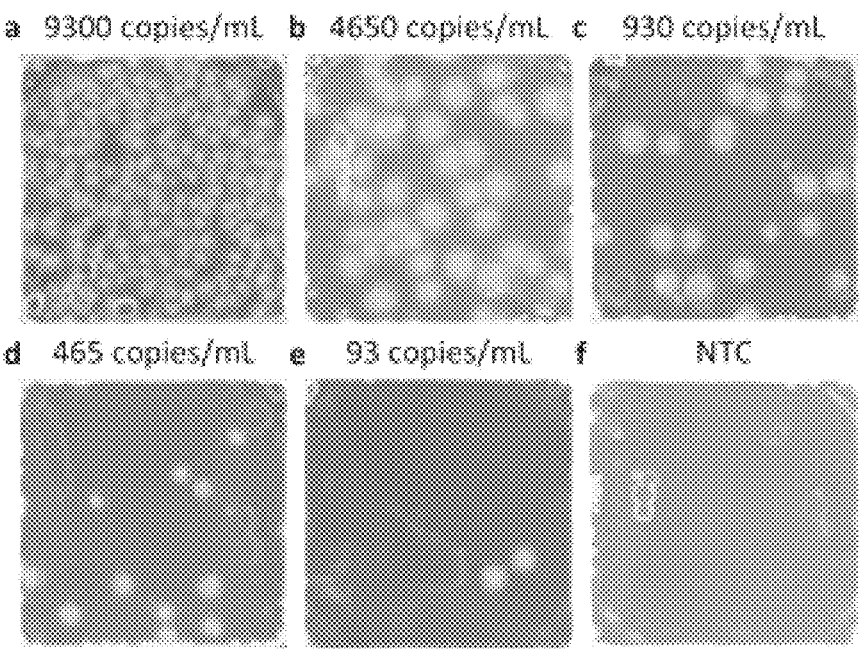
FIGS. 14A-F show example photos of finished mgLAMP slides taken by a smartphone, for varying concentrations of SARS-CoV-2 spiked surface water.

FIGS. 14 and 15 show experimental test results of an example of the mgLAMP process for SARS-CoV-2 spiked surface water. FIGS. 14A-F show example photos of finished mgLAMP slides taken by a smartphone under illumination, for varying concentrations of SARS-CoV-2 spiked surface water. As seen in FIGS. 14A-E, no significant difference on the amplicon dot size was observed between different template concentrations ranging from 93 copies/mL to 4650 copies/mL. Although the amplicon dot size was significantly decreased at a template concentration of 9300 copies/mL, the dots were still with well-defined boundaries. As shown by the graph in FIG. 15, mgLAMP showed a significant linear correlation ($R^2$=0.9565) between the copies/mL in the matrix of surface water. For surface water with SARS-CoV-2 spiked at the concentration of 930 copies/mL, RT-qPCR combined with an optimal sample preparation process of adding 25 mM $MgCl_2$ was completely inhibited, as reported elsewhere. Thus, the LOD of mgLAMP for SARS-CoV-2 detection in surface water matrix, as tested, was at least 10-fold lower than that of a known RT-qPCR method.

In SARS-CoV-2 particle-spiked Milli-Q water, performance of an mgLAMP technique disclosed herein was compared with an RT-qPCR standard. The MgLAMP technique achieved an LOD of 0.96 copies/mL from 100 mL water, with a dynamic range covering up to 9600 copies/mL. Compared to RT-qPCR, the disclosed mgLAMP techniques have the advantage of simplified sample processing, minimal instrumentation requirements, an absolute quantification capability, and a much lower LOD due to the integrated viral concentration. At high viral loads, the accuracy of the disclosed techniques benefited from the clarity of the boundaries between amplicon dots. To examine the boundary of closely located dots, a z-stack process to construct a 3D image of three closely located amplicon dots may be performed in some embodiments. The z-direction represents the depth across the frame-seal chamber with the PCTE membrane sitting at around z=0. The absence of viral particle aggregation during filtration may allow ample space between RNA templates for amplicon dot growth through amplification and diffusion of products. Compared to other in-gel amplification in published studies where extracted nucleic acid was spiked, the amplicon dots in the disclosed mg LAMP techniques may feature clearer boundaries between adjacent dots, which may be due to the horizontal distribution of targets without entanglement or z-overlap.

Any of the assay systems, e.g., system 10, or methods, e.g., methods 40, 100, disclosed herein may be employed for efficient detection and/or monitoring of microorganisms such as viral particles, viruses, bacteriophages, protozoa, bacteria, or any combination of the foregoing, and the like in any suitable sample, for example, a water or food sample, or biological sample.

For example, in some embodiments, the methods and systems disclosed herein have also demonstrated to be capable for bacterial detection and quantification of *Escherichia coli* (*E. coli*) and *Salmonella typhi* (*S. typhi*).

Table 6 shows example primer sequences for *E. coli* and *S. typhi* that may be used with the mgLAMP methods and systems disclosed herein.

TABLE 6

| Target | Primer name | Sequence (5'-3') |
|--------|-------------|------------------|
| *E. coli* | F3 | GCCATCTCCTGATGACGC (SEQ ID NO: 75) |
| | B3 | ATTTACCGCAGCCAGACG (SEQ ID NO: 76) |
| | FIP | CATTTTGCAGCTGTACGC TCGCAGCCCATCATGAAT GTTGCT (SEQ ID NO: 77) |

TABLE 6-continued

| Target | Primer name | Sequence (5'-3') |
|---|---|---|
| | BIP | CTGGGGCGAGGTCGTGG TATTCCGACAAACACCA CGAATT (SEQ ID NO: 78) |
| | LF | CTTTGTAACAACCTGTC ATCGACA (SEQ ID NO: 79) |
| | LB | ATCAATCTCGATATCCA TGAAGGTG (SEQ ID NO: 80) |
| S. Typhi | F3 | GACTTGCCTTTAAAAGA TACCA (SEQ ID NO: 81) |
| | B3 | AGAGTGCGTTTGAACAC TT (SEQ ID NO: 82) |
| | FIP | AACTTGCTGCTGAAGAG TTGGACCGAATGACTCG ACCAT C (SEQ ID NO: 83) |
| | BIP | CCTGGGGCCAAATGGCA TTATGCACTAAGTAAGG CTGG (SEQ ID NO: 84) |
| | LF | TCGGATGGCTTCGTTCC T (SEQ ID NO: 85) |
| | LB | CAAGGGTTTCAAGACT AAGTGGTTC (SEQ ID NO: 86) |

For example, the LODs using mgLAMP for *Escherichia coli* (*E. coli*) and *Salmonella typhi* (*S. typhi*) in Milli-Q water are as low as 40 cells/mL using the methods and systems described herein. The versatility of mgLAMP approach should be suitable for analysis of other pathogens (e.g., influenza) quantification in general.

The disclosure provides various embodiments. One of skill in the art will recognize that certain other embodiments, preparations and steps are compatible with the disclosed invention.

A number of samples are consistent with the methods, reagents, and devices disclosed herein. These samples can comprise a target nucleic acid from various organisms for detection (e.g., SARS-CoV-2). Generally, a sample from an individual or an animal, or an environmental sample can be obtained to test for presence of, e.g., SARS-CoV-2. A biological sample from the individual may be a sample selected from blood, serum, plasma, saliva, urine, mucosal, peritoneal, cerebrospinal, gastric secretions, nasal secretions, sputum, pharyngeal exudates, urethral or vaginal secretions, an exudate, an effusion, or tissue. A tissue sample may be dissociated or liquefied prior to use in the methods of the disclosure. A sample from an environment may be from soil, air or water. In some instances, the environmental sample is collected by using a swab. In a particular embodiment, the sample is unprocessed and used directly in the methods of the disclosure. In another embodiment, the sample is diluted with a buffer or a fluid or concentrated prior to application to the detection system or be applied neat to the detection system. Sometimes, less than 20 µL of the sample is used in the methods of the disclosure. The sample in some embodiments is in a volume of 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL, 200 µL, 300 µL, 400 µL, 500 µL, or a range that includes or is between any two of the foregoing values.

A number of target nucleic acids from a microorganism to be detected, e.g., SARS-CoV-2, can be used in the methods disclosed herein. The methods of the disclosure can detect a target nucleic acid present in the sample in various concentrations or amounts as a target nucleic acid. In some cases, the sample has at least 2 target nucleic acids. In some cases, the sample has 3, 5, 10, 20, 30, 40, 50, 60, 70, 80, 90, 100, 150, 200, 250, 300, 350, 400, 450, 500, 750, 1000, 2000, 3000, 4000, 5000, 6000, 7000, 8000, 9000, or 10,000 target nucleic acids. In some cases, the method detects target nucleic acids present at rate of one copy per $10^1$ non-target nucleic acids, $10^2$ non-target nucleic acids, $10^3$ non-target nucleic acids, $10^4$ non-target nucleic acids, $10^5$ non-target nucleic acids, $10^6$ non-target nucleic acids, $10^7$ non-target nucleic acids, $10^8$ non-target nucleic acids, $10^9$ non-target nucleic acids, $10^{10}$ non-target nucleic acids, or a range that includes or is between any two of the foregoing values.

A number of target nucleic acids can be amplified and are consistent with the methods or compositions disclosed herein. In a particular embodiment, the methods of the disclosure detect two or more target nucleic acid sequences present in the sample in various concentrations or amounts. In some cases, the sample has at least 2 target nucleic acid sequences from SARS-CoV-2. In other cases, the sample has at least 3, 4, 5, 6, 7, 8, 9, 10, 20, 30, 40, 50 target nucleic acid sequences from SARS-CoV-2, or a range that includes or is between any two of the foregoing values.

The foregoing description is illustrative and not restrictive. Although certain exemplary embodiments have been described, other embodiments, combinations and modifications involving the invention will occur readily to those of ordinary skill in the art in view of the foregoing teachings. Therefore, this invention is to be limited only by the following claims, which cover at least some of the disclosed embodiments, as well as all other such embodiments and modifications when viewed in conjunction with the above specification and accompanying drawings.

What is claimed is:

1. A system for detecting a target microorganism in a sample suspected of containing the target microorganism, comprising:

one or more primary filters configured to remove particles larger than the target microorganism from the sample, whereby producing a primary filtered sample;

a filter membrane receiving the primary filtered sample and configured to trap the target microorganism on a membrane while passing through the membrane particles present in the primary filtered sample that are smaller than the target microorganism;

loop mediated isothermal amplification (LAMP) reagents;

hydrogel components;

a microorganism lysis agent;

an openable plastic reagent pouch containing the LAMP reagents, the microorganism lysis agent in liquid form and one or more breakable capsules containing a dry, powder form of the hydrogel components, wherein the openable plastic pouch is configured to allow a user to mix the LAMP reagents, the lysis agent, and the hydrogel components in the pouch to form a mixture and then open the pouch to apply the mixture to the filter membrane;

a transparent substrate configured to receive the filter membrane with the mixture having been applied thereto, whereby forming a loaded substrate;

an incubator configured to heat the loaded substrate;

a fluorescence illuminator configured to illuminate the loaded substrate;

wherein the substrate allows visual detection of the presence or absence of one or more fluorescent amplicons that are produced as a result of a LAMP reaction amplifying the DNA or RNA of the target microorganism if the target microorganism is present on the membrane, wherein the presence of the amplicons is indicative of the presence of the target microorganism in the sample and the absence of the amplicons is indicative of the absence of the target microorganism in the sample.

2. The system of claim 1, wherein the LAMP reagents include a fluro-primer and primer-quencher duplex.

3. The system of claim 1, wherein the microorganism lysis agent is a non-ionic detergent.

4. The system of claim 3, wherein the microorganism lysis agent is t-Octylphenoxypolyethoxyethanol at 0.5% v/v.

5. The system of claim 1, further comprising a reagent pouch containing 5% w/v of the hydrogel components, 0.5% v/v of a lysis agent, 1 U/μL RNase Inhibitor Murine, 0.02 U/μL Antarctic Thermolabile UDG, 700 μM of dUTP solution, a primer set comprising: 1.6 μM of FIP, 1.6 μM of 5' FAM-BIP, 0.2 μM of F3, 0.2 μM of B3, 0.4 μM of LB, and 2.4 μM of qBIP15nt, and nuclease-free water.

6. The system of claim 1, wherein the hydrogel components include 4-arm polyethylene glycol (PEG) acrylate and thiol-PEG-thiol ($SHCH_2CH_2O(CH_2CH_2O)_nCH_2CH_2SH$).

7. The system of claim 1, wherein a hydrogel is formed through a thiol-Michael addition reaction between 4-arm polyethylene glycol (PEG) acrylate having a molecular weight of 10 K and thiol-PEG-thiol ($SHCH_2CH_2O$ $(CH_2CH_2O)_nCH_2CH_2SH$) having a molecular weight of 3.4 K at a molar ratio of 1:2 of 4-arm PEG acrylate to thiol-PEG-thiol.

8. The system of claim 1, wherein the filter membrane is a porous track-etched polycarbonate (PCTE) membrane having a pore size of 80 nm or less.

9. The system of claim 1, further comprising a portable device that includes:

the incubator;

the fluorescence illuminator; and a housing having a plurality of slots for receiving a plurality of loaded slides and a viewing port for permitting visual inspection of the loaded slides.

10. The system of claim 9, wherein the portable device further comprises a user interface and controller configured to receive user selections of incubator heating temperature, incubator heating duration, and fluorescence illuminator activation.

11. The system of claim 9, wherein the housing includes:

an incubator compartment housing the incubator;

an illuminator compartment, located above the incubator compartment, housing the fluorescence illuminator;

a first plurality of slots, formed in a side of the housing and opening into the incubator compartment, configured to admit a plurality of loaded slides into the incubator compartment; and a second plurality of slots, formed in a side of the housing and opening into the illuminator compartment, configured to admit a plurality of loaded slides into the illuminator compartment.

12. The system of claim 1, further comprising a camera configured to capture an image of the loaded substrate.

13. The system of claim 12, further comprising a machine learning model computer program, executable by a processor, for identifying and counting fluorescent amplicons in the captured image.

14. The system of claim 13, wherein the camera is included in a smartphone configured to communicate with a remote server by way of a computer network, wherein the machine learning model computer program is executed by the remote server.

15. The system of claim 1, further comprising:

means for sonicating the sample to separate the target microorganism from other particles in the sample.

16. The system of claim 1, wherein the sample is selected from the group consisting of environmental water and wastewater.

17. The system of claim 1, wherein the microorganism is a SARS-Cov-2 virus.

* * * * *

SEQUENCE LISTING

```
<160> NUMBER OF SEQ ID NOS: 86

<210> SEQ ID NO 1
<211> LENGTH: 23
<212> TYPE: DNA
<213> ORGANISM: Artificial Sequence
<220> FEATURE:
```

<223> OTHER INFORMATION: F3 Primer N gene

<400> SEQUENCE: 1
gtcattttgc tgaataagca tat                                           23

<210> SEQ ID NO 2
<211> LENGTH: 18
<212> TYPE: DNA
<213> ORGANISM: Artificial Sequence
<220> FEATURE:
<223> OTHER INFORMATION: B3 Primer N gene

<400> SEQUENCE: 2
gagtcagcac tgctcatg                                                 18

<210> SEQ ID NO 3
<211> LENGTH: 44
<212> TYPE: DNA
<213> ORGANISM: Artificial Sequence
<220> FEATURE:
<223> OTHER INFORMATION: FIP Primer N gene

<400> SEQUENCE: 3
taaggcttga gtttcatcag ccttacgcat acaaaacatt ccca                    44

<210> SEQ ID NO 4
<211> LENGTH: 45
<212> TYPE: DNA
<213> ORGANISM: Artificial Sequence
<220> FEATURE:
<223> OTHER INFORMATION: BIP Primer N gene

<400> SEQUENCE: 4
cagagacaga agaaacagca aactgattgt tgcaattgtt tggag                   45

<210> SEQ ID NO 5
<211> LENGTH: 25
<212> TYPE: DNA
<213> ORGANISM: Artificial Sequence
<220> FEATURE:
<223> OTHER INFORMATION: LB Primer N gene

<400> SEQUENCE: 5
gtgactcttc ttcctgctgc agatt                                         25

<210> SEQ ID NO 6
<211> LENGTH: 15
<212> TYPE: DNA
<213> ORGANISM: Artificial Sequence
<220> FEATURE:
<223> OTHER INFORMATION: FAM-BIP

<400> SEQUENCE: 6
tttcttctgt ctctg                                                    15

<210> SEQ ID NO 7
<211> LENGTH: 18
<212> TYPE: DNA
<213> ORGANISM: Artificial Sequence
<220> FEATURE:
<223> OTHER INFORMATION: F3 Primer N gene

<400> SEQUENCE: 7
tggaccccaa aatcagcg                                                 18

```
<210> SEQ ID NO 8
<211> LENGTH: 19
<212> TYPE: DNA
<213> ORGANISM: Artificial Sequence
<220> FEATURE:
<223> OTHER INFORMATION: B3 Primer N gene

<400> SEQUENCE: 8
gccttgtcct cgagggaat                                                   19

<210> SEQ ID NO 9
<211> LENGTH: 41
<212> TYPE: DNA
<213> ORGANISM: Artificial Sequence
<220> FEATURE:
<223> OTHER INFORMATION: FIP Primer N gene

<400> SEQUENCE: 9
ccactgcgtt ctccattctg gtaaatgcac cccgcattac g                          41

<210> SEQ ID NO 10
<211> LENGTH: 41
<212> TYPE: DNA
<213> ORGANISM: Artificial Sequence
<220> FEATURE:
<223> OTHER INFORMATION: BIP Primer N gene

<400> SEQUENCE: 10
cgcgatcaaa acaacgtcgg cccttgccat gttgagtgag a                          41

<210> SEQ ID NO 11
<211> LENGTH: 20
<212> TYPE: DNA
<213> ORGANISM: Artificial Sequence
<220> FEATURE:
<223> OTHER INFORMATION: LF Primer N gene

<400> SEQUENCE: 11
tgaatctgag ggtccaccaa                                                  20

<210> SEQ ID NO 12
<211> LENGTH: 25
<212> TYPE: DNA
<213> ORGANISM: Artificial Sequence
<220> FEATURE:
<223> OTHER INFORMATION: LB Primer N gene

<400> SEQUENCE: 12
ttacccaata atactgcgtc ttggt                                            25

<210> SEQ ID NO 13
<211> LENGTH: 20
<212> TYPE: DNA
<213> ORGANISM: Artificial Sequence
<220> FEATURE:
<223> OTHER INFORMATION: F3 Primer N gene

<400> SEQUENCE: 13
ccagaatgga gaacgcagtg                                                  20

<210> SEQ ID NO 14
<211> LENGTH: 18
<212> TYPE: DNA
<213> ORGANISM: Artificial Sequence
<220> FEATURE:
<223> OTHER INFORMATION: B3 Primer N gene
```

<400> SEQUENCE: 14
ccgtcaccac cacgaatt                                              18

<210> SEQ ID NO 15
<211> LENGTH: 38
<212> TYPE: DNA
<213> ORGANISM: Artificial Sequence
<220> FEATURE:
<223> OTHER INFORMATION: FIP Primer N gene

<400> SEQUENCE: 15
agcggtgaac caagacgcag ggcgcgatca aaacaacg                        38

<210> SEQ ID NO 16
<211> LENGTH: 41
<212> TYPE: DNA
<213> ORGANISM: Artificial Sequence
<220> FEATURE:
<223> OTHER INFORMATION: BIP Primer N gene

<400> SEQUENCE: 16
aattccctcg aggacaaggc gagctcttcg gtagtagcca a                    41

<210> SEQ ID NO 17
<211> LENGTH: 21
<212> TYPE: DNA
<213> ORGANISM: Artificial Sequence
<220> FEATURE:
<223> OTHER INFORMATION: LF Primer N gene

<400> SEQUENCE: 17
ttattgggta aaccttgggg c                                          21

<210> SEQ ID NO 18
<211> LENGTH: 24
<212> TYPE: DNA
<213> ORGANISM: Artificial Sequence
<220> FEATURE:
<223> OTHER INFORMATION: LB Primer N gene

<400> SEQUENCE: 18
taacaccaat agcagtccag atga                                       24

<210> SEQ ID NO 19
<211> LENGTH: 21
<212> TYPE: DNA
<213> ORGANISM: Artificial Sequence
<220> FEATURE:
<223> OTHER INFORMATION: F3 Primer ORF1ab

<400> SEQUENCE: 19
tccagatgag gatgaagaag a                                          21

<210> SEQ ID NO 20
<211> LENGTH: 21
<212> TYPE: DNA
<213> ORGANISM: Artificial Sequence
<220> FEATURE:
<223> OTHER INFORMATION: B3 Primer ORF1ab

<400> SEQUENCE: 20
agtctgaaca actggtgtaa g                                          21

<210> SEQ ID NO 21
<211> LENGTH: 41

-continued

```
<212> TYPE: DNA
<213> ORGANISM: Artificial Sequence
<220> FEATURE:
<223> OTHER INFORMATION: FIP Primer ORF1ab

<400> SEQUENCE: 21
agagcagcag aagtggcaca ggtgattgtg aagaagaaga g                    41

<210> SEQ ID NO 22
<211> LENGTH: 40
<212> TYPE: DNA
<213> ORGANISM: Artificial Sequence
<220> FEATURE:
<223> OTHER INFORMATION: BIP Primer ORF1ab

<400> SEQUENCE: 22
tcaacctgaa gaagagcaag aactgattgt cctcactgcc                     40

<210> SEQ ID NO 23
<211> LENGTH: 22
<212> TYPE: DNA
<213> ORGANISM: Artificial Sequence
<220> FEATURE:
<223> OTHER INFORMATION: LF Primer ORF1ab

<400> SEQUENCE: 23
ctcatattga gttgatggct ca                                        22

<210> SEQ ID NO 24
<211> LENGTH: 22
<212> TYPE: DNA
<213> ORGANISM: Artificial Sequence
<220> FEATURE:
<223> OTHER INFORMATION: LB Primer ORF1ab

<400> SEQUENCE: 24
acaaactgtt ggtcaacaag ac                                        22

<210> SEQ ID NO 25
<211> LENGTH: 20
<212> TYPE: DNA
<213> ORGANISM: Artificial Sequence
<220> FEATURE:
<223> OTHER INFORMATION: F3 Primer ORF1a

<400> SEQUENCE: 25
ctgcacctca tggtcatgtt                                           20

<210> SEQ ID NO 26
<211> LENGTH: 19
<212> TYPE: DNA
<213> ORGANISM: Artificial Sequence
<220> FEATURE:
<223> OTHER INFORMATION: B3 Primer ORF1a

<400> SEQUENCE: 26
agctcgtcgc ctaagtcaa                                            19

<210> SEQ ID NO 27
<211> LENGTH: 42
<212> TYPE: DNA
<213> ORGANISM: Artificial Sequence
<220> FEATURE:
<223> OTHER INFORMATION: FIP Primer ORF1a

<400> SEQUENCE: 27
```

-continued gagggacaag gacaccaagt gtatggttga gctggtagca ga                    42

<210> SEQ ID NO 28
<211> LENGTH: 39
<212> TYPE: DNA
<213> ORGANISM: Artificial Sequence
<220> FEATURE:
<223> OTHER INFORMATION: BIP Primer ORF1a

<400> SEQUENCE: 28
ccagtggctt accgcaaggt tttagatcgg cgccgtaac                        39

<210> SEQ ID NO 29
<211> LENGTH: 21
<212> TYPE: DNA
<213> ORGANISM: Artificial Sequence
<220> FEATURE:
<223> OTHER INFORMATION: LF Primer ORF1a

<400> SEQUENCE: 29
ccgtactgaa tgccttcgag t                                          21

<210> SEQ ID NO 30
<211> LENGTH: 25
<212> TYPE: DNA
<213> ORGANISM: Artificial Sequence
<220> FEATURE:
<223> OTHER INFORMATION: LB Primer ORF1a

<400> SEQUENCE: 30
ttcgtaagaa cggtaataaa ggagc                                      25

<210> SEQ ID NO 31
<211> LENGTH: 20
<212> TYPE: DNA
<213> ORGANISM: Artificial Sequence
<220> FEATURE:
<223> OTHER INFORMATION: F3 Primer ORF1a

<400> SEQUENCE: 31
tcatcaaacg ttcggatgct                                            20

<210> SEQ ID NO 32
<211> LENGTH: 18
<212> TYPE: DNA
<213> ORGANISM: Artificial Sequence
<220> FEATURE:
<223> OTHER INFORMATION: B3 Primer ORF1a

<400> SEQUENCE: 32
tatggccacc agctcctt                                              18

<210> SEQ ID NO 33
<211> LENGTH: 42
<212> TYPE: DNA
<213> ORGANISM: Artificial Sequence
<220> FEATURE:
<223> OTHER INFORMATION: FIP Primer ORF1a

<400> SEQUENCE: 33
cgaccgtact gaatgccttc gagaactgca cctcatggtc at                    42

<210> SEQ ID NO 34
<211> LENGTH: 42
<212> TYPE: DNA
<213> ORGANISM: Artificial Sequence

```
<220> FEATURE:
<223> OTHER INFORMATION: BIP Primer ORF1a

<400> SEQUENCE: 34
agacacttgg tgtccttgtc ccagaagaac cttgcggtaa gc                        42

<210> SEQ ID NO 35
<211> LENGTH: 22
<212> TYPE: DNA
<213> ORGANISM: Artificial Sequence
<220> FEATURE:
<223> OTHER INFORMATION: LF Primer ORF1a

<400> SEQUENCE: 35
ctgctaccag ctcaaccata ac                                             22

<210> SEQ ID NO 36
<211> LENGTH: 21
<212> TYPE: DNA
<213> ORGANISM: Artificial Sequence
<220> FEATURE:
<223> OTHER INFORMATION: LB Primer ORF1a

<400> SEQUENCE: 36
tcatgtgggc gaaataccag t                                              21

<210> SEQ ID NO 37
<211> LENGTH: 20
<212> TYPE: DNA
<213> ORGANISM: Artificial Sequence
<220> FEATURE:
<223> OTHER INFORMATION: F3 Primer ORF1a

<400> SEQUENCE: 37
ctgcacctca tggtcatgtt                                                20

<210> SEQ ID NO 38
<211> LENGTH: 19
<212> TYPE: DNA
<213> ORGANISM: Artificial Sequence
<220> FEATURE:
<223> OTHER INFORMATION: B3 Primer ORF1a

<400> SEQUENCE: 38
gatcagtgcc aagctcgtc                                                 19

<210> SEQ ID NO 39
<211> LENGTH: 41
<212> TYPE: DNA
<213> ORGANISM: Artificial Sequence
<220> FEATURE:
<223> OTHER INFORMATION: FIP Primer ORF1a

<400> SEQUENCE: 39
gagggacaag gacaccaagt gtggtagcag aactcgaagg c                        41

<210> SEQ ID NO 40
<211> LENGTH: 39
<212> TYPE: DNA
<213> ORGANISM: Artificial Sequence
<220> FEATURE:
<223> OTHER INFORMATION: BIP Primer ORF1a

<400> SEQUENCE: 40
ccagtggctt accgcaaggt tttagatcgg cgccgtaac                           39
```

-continued

```
<210> SEQ ID NO 41
<211> LENGTH: 21
<212> TYPE: DNA
<213> ORGANISM: Artificial Sequence
<220> FEATURE:
<223> OTHER INFORMATION: LF Primer ORF1a

<400> SEQUENCE: 41
accactacga ccgtactgaa t                                              21

<210> SEQ ID NO 42
<211> LENGTH: 25
<212> TYPE: DNA
<213> ORGANISM: Artificial Sequence
<220> FEATURE:
<223> OTHER INFORMATION: LB Primer ORF1a

<400> SEQUENCE: 42
ttcgtaagaa cggtaataaa ggagc                                          25

<210> SEQ ID NO 43
<211> LENGTH: 19
<212> TYPE: DNA
<213> ORGANISM: Artificial Sequence
<220> FEATURE:
<223> OTHER INFORMATION: F3 Primer N gene

<400> SEQUENCE: 43
tggctactac cgaagagct                                                 19

<210> SEQ ID NO 44
<211> LENGTH: 20
<212> TYPE: DNA
<213> ORGANISM: Artificial Sequence
<220> FEATURE:
<223> OTHER INFORMATION: B3 Primer N gene

<400> SEQUENCE: 44
tgcagcattg ttagcaggat                                                20

<210> SEQ ID NO 45
<211> LENGTH: 41
<212> TYPE: DNA
<213> ORGANISM: Artificial Sequence
<220> FEATURE:
<223> OTHER INFORMATION: FIP Primer N gene

<400> SEQUENCE: 45
tctggcccag ttcctaggta gtccagacga attcgtggtg g                        41

<210> SEQ ID NO 46
<211> LENGTH: 40
<212> TYPE: DNA
<213> ORGANISM: Artificial Sequence
<220> FEATURE:
<223> OTHER INFORMATION: BIP Primer N gene

<400> SEQUENCE: 46
agacggcatc atatgggttg cacgggtgcc aatgtgatct                          40

<210> SEQ ID NO 47
<211> LENGTH: 25
<212> TYPE: DNA
<213> ORGANISM: Artificial Sequence
<220> FEATURE:
<223> OTHER INFORMATION: LF Primer N gene
```

-continued

```
<400> SEQUENCE: 47
ggactgagat ctttcatttt accgt                                            25

<210> SEQ ID NO 48
<211> LENGTH: 21
<212> TYPE: DNA
<213> ORGANISM: Artificial Sequence
<220> FEATURE:
<223> OTHER INFORMATION: LB Primer N gene

<400> SEQUENCE: 48
actgagggag ccttgaatac a                                                21

<210> SEQ ID NO 49
<211> LENGTH: 19
<212> TYPE: DNA
<213> ORGANISM: Artificial Sequence
<220> FEATURE:
<223> OTHER INFORMATION: F3 Primer N gene

<400> SEQUENCE: 49
accgaagagc taccagacg                                                   19

<210> SEQ ID NO 50
<211> LENGTH: 20
<212> TYPE: DNA
<213> ORGANISM: Artificial Sequence
<220> FEATURE:
<223> OTHER INFORMATION: B3 Primer N gene

<400> SEQUENCE: 50
tgcagcattg ttagcaggat                                                  20

<210> SEQ ID NO 51
<211> LENGTH: 40
<212> TYPE: DNA
<213> ORGANISM: Artificial Sequence
<220> FEATURE:
<223> OTHER INFORMATION: FIP Primer N gene

<400> SEQUENCE: 51
tctggcccag ttcctaggta gttcgtggtg gtgacggtaa                            40

<210> SEQ ID NO 52
<211> LENGTH: 40
<212> TYPE: DNA
<213> ORGANISM: Artificial Sequence
<220> FEATURE:
<223> OTHER INFORMATION: BIP Primer N gene

<400> SEQUENCE: 52
agacggcatc atatgggttg cacgggtgcc aatgtgatct                            40

<210> SEQ ID NO 53
<211> LENGTH: 25
<212> TYPE: DNA
<213> ORGANISM: Artificial Sequence
<220> FEATURE:
<223> OTHER INFORMATION: LF Primer N gene

<400> SEQUENCE: 53
ccatcttgga ctgagatctt tcatt                                            25

<210> SEQ ID NO 54
```

<211> LENGTH: 21
<212> TYPE: DNA
<213> ORGANISM: Artificial Sequence
<220> FEATURE:
<223> OTHER INFORMATION: LB Primer N gene

<400> SEQUENCE: 54
actgagggag ccttgaatac a                                              21

<210> SEQ ID NO 55
<211> LENGTH: 18
<212> TYPE: DNA
<213> ORGANISM: Artificial Sequence
<220> FEATURE:
<223> OTHER INFORMATION: F3 Primer ORF1ab

<400> SEQUENCE: 55
tgcttcagtc agctgatg                                                  18

<210> SEQ ID NO 56
<211> LENGTH: 22
<212> TYPE: DNA
<213> ORGANISM: Artificial Sequence
<220> FEATURE:
<223> OTHER INFORMATION: B3 Primer ORF1ab

<400> SEQUENCE: 56
ttaaattgtc atcttcgtcc tt                                             22

<210> SEQ ID NO 57
<211> LENGTH: 41
<212> TYPE: DNA
<213> ORGANISM: Artificial Sequence
<220> FEATURE:
<223> OTHER INFORMATION: FIP Primer ORF1ab

<400> SEQUENCE: 57
tcagtactag tgcctgtgcc cacaatcgtt tttaaacggg t                        41

<210> SEQ ID NO 58
<211> LENGTH: 43
<212> TYPE: DNA
<213> ORGANISM: Artificial Sequence
<220> FEATURE:
<223> OTHER INFORMATION: BIP Primer ORF1ab

<400> SEQUENCE: 58
tcgtatacag ggcttttgac atctatcttg gaagcgacaa caa                      43

<210> SEQ ID NO 59
<211> LENGTH: 17
<212> TYPE: DNA
<213> ORGANISM: Artificial Sequence
<220> FEATURE:
<223> OTHER INFORMATION: LF Primer ORF1ab

<400> SEQUENCE: 59
ctgcacttac accgcaa                                                   17

<210> SEQ ID NO 60
<211> LENGTH: 22
<212> TYPE: DNA
<213> ORGANISM: Artificial Sequence
<220> FEATURE:
<223> OTHER INFORMATION: LB Primer ORF1ab

<400> SEQUENCE: 60

-continued gtagctggtt ttgctaaatt cc                                                22

<210> SEQ ID NO 61
<211> LENGTH: 19
<212> TYPE: DNA
<213> ORGANISM: Artificial Sequence
<220> FEATURE:
<223> OTHER INFORMATION: F3 Primer N gene

<400> SEQUENCE: 61
gttcctcatc acgtagtcg                                                    19

<210> SEQ ID NO 62
<211> LENGTH: 19
<212> TYPE: DNA
<213> ORGANISM: Artificial Sequence
<220> FEATURE:
<223> OTHER INFORMATION: B3 Primer N gene

<400> SEQUENCE: 62
gtttggcctt gttgttgtt                                                    19

<210> SEQ ID NO 63
<211> LENGTH: 43
<212> TYPE: DNA
<213> ORGANISM: Artificial Sequence
<220> FEATURE:
<223> OTHER INFORMATION: FIP Primer N gene

<400> SEQUENCE: 63
gccagccatt ctagcaggag caacagttaa gaaattcaac tcc                        43

<210> SEQ ID NO 64
<211> LENGTH: 40
<212> TYPE: DNA
<213> ORGANISM: Artificial Sequence
<220> FEATURE:
<223> OTHER INFORMATION: BIP Primer N gene

<400> SEQUENCE: 64
gatgctgctc ttgctttgct accagacatt ttgctctcaa                            40

<210> SEQ ID NO 65
<211> LENGTH: 22
<212> TYPE: DNA
<213> ORGANISM: Artificial Sequence
<220> FEATURE:
<223> OTHER INFORMATION: LB Primer N gene

<400> SEQUENCE: 65
gctgcttgac agattgaacc ag                                                22

<210> SEQ ID NO 66
<211> LENGTH: 23
<212> TYPE: DNA
<213> ORGANISM: Artificial Sequence
<220> FEATURE:
<223> OTHER INFORMATION: F3 Primer N gene

<400> SEQUENCE: 66
gtcattttgc tgaataagca tat                                               23

<210> SEQ ID NO 67
<211> LENGTH: 18
<212> TYPE: DNA

-continued

```
<213> ORGANISM: Artificial Sequence
<220> FEATURE:
<223> OTHER INFORMATION: B3 Primer N gene

<400> SEQUENCE: 67
gagtcagcac tgctcatg                                                    18

<210> SEQ ID NO 68
<211> LENGTH: 44
<212> TYPE: DNA
<213> ORGANISM: Artificial Sequence
<220> FEATURE:
<223> OTHER INFORMATION: FIP Primer N gene

<400> SEQUENCE: 68
taaggcttga gtttcatcag ccttacgcat acaaaacatt ccca                       44

<210> SEQ ID NO 69
<211> LENGTH: 45
<212> TYPE: DNA
<213> ORGANISM: Artificial Sequence
<220> FEATURE:
<223> OTHER INFORMATION: BIP Primer N gene

<400> SEQUENCE: 69
cagagacaga agaaacagca aactgattgt tgcaattgtt tggag                      45

<210> SEQ ID NO 70
<211> LENGTH: 25
<212> TYPE: DNA
<213> ORGANISM: Artificial Sequence
<220> FEATURE:
<223> OTHER INFORMATION: LB Primer N gene

<400> SEQUENCE: 70
gtgactcttc ttcctgctgc agatt                                            25

<210> SEQ ID NO 71
<211> LENGTH: 15
<212> TYPE: DNA
<213> ORGANISM: Artificial Sequence
<220> FEATURE:
<223> OTHER INFORMATION: QFIP 12nt probe

<400> SEQUENCE: 71
tttcttctgt ctctg                                                       15

<210> SEQ ID NO 72
<211> LENGTH: 17
<212> TYPE: DNA
<213> ORGANISM: Artificial Sequence
<220> FEATURE:
<223> OTHER INFORMATION: qFIP17nt probe

<400> SEQUENCE: 72
atgaaactca agcctta                                                     17

<210> SEQ ID NO 73
<211> LENGTH: 10
<212> TYPE: DNA
<213> ORGANISM: Artificial Sequence
<220> FEATURE:
<223> OTHER INFORMATION: qBIP10nt probe

<400> SEQUENCE: 73
tctgtctctg                                                             10
```

```
<210> SEQ ID NO 74
<211> LENGTH: 15
<212> TYPE: DNA
<213> ORGANISM: Artificial Sequence
<220> FEATURE:
<223> OTHER INFORMATION: qBIP15nt probe

<400> SEQUENCE: 74
tttcttctgt ctctg                                             15

<210> SEQ ID NO 75
<211> LENGTH: 18
<212> TYPE: DNA
<213> ORGANISM: Artificial Sequence
<220> FEATURE:
<223> OTHER INFORMATION: F3 Primer E.coli

<400> SEQUENCE: 75
gccatctcct gatgacgc                                          18

<210> SEQ ID NO 76
<211> LENGTH: 18
<212> TYPE: DNA
<213> ORGANISM: Artificial Sequence
<220> FEATURE:
<223> OTHER INFORMATION: B3 Primer E.coli

<400> SEQUENCE: 76
atttaccgca gccagacg                                          18

<210> SEQ ID NO 77
<211> LENGTH: 42
<212> TYPE: DNA
<213> ORGANISM: Artificial Sequence
<220> FEATURE:
<223> OTHER INFORMATION: FIP Primer E.coli

<400> SEQUENCE: 77
cattttgcag ctgtacgctc gcagcccatc atgaatgttg ct               42

<210> SEQ ID NO 78
<211> LENGTH: 40
<212> TYPE: DNA
<213> ORGANISM: Artificial Sequence
<220> FEATURE:
<223> OTHER INFORMATION: BIP Primer E.coli

<400> SEQUENCE: 78
ctggggcgag gtcgtggtat tccgacaaac accacgaatt                  40

<210> SEQ ID NO 79
<211> LENGTH: 24
<212> TYPE: DNA
<213> ORGANISM: Artificial Sequence
<220> FEATURE:
<223> OTHER INFORMATION: LF Primer E.coli

<400> SEQUENCE: 79
ctttgtaaca acctgtcatc gaca                                   24

<210> SEQ ID NO 80
<211> LENGTH: 25
<212> TYPE: DNA
<213> ORGANISM: Artificial Sequence
<220> FEATURE:
```

<223> OTHER INFORMATION: LB Primer E.coli

<400> SEQUENCE: 80
atcaatctcg atatccatga aggtg                                          25

<210> SEQ ID NO 81
<211> LENGTH: 22
<212> TYPE: DNA
<213> ORGANISM: Artificial Sequence
<220> FEATURE:
<223> OTHER INFORMATION: F3 Primer S.typhi

<400> SEQUENCE: 81
gacttgcctt taaaagatac ca                                             22

<210> SEQ ID NO 82
<211> LENGTH: 19
<212> TYPE: DNA
<213> ORGANISM: Artificial Sequence
<220> FEATURE:
<223> OTHER INFORMATION: B3 Primer S.typhi

<400> SEQUENCE: 82
agagtgcgtt tgaacactt                                                 19

<210> SEQ ID NO 83
<211> LENGTH: 40
<212> TYPE: DNA
<213> ORGANISM: Artificial Sequence
<220> FEATURE:
<223> OTHER INFORMATION: FIP Primer S.typhi

<400> SEQUENCE: 83
aacttgctgc tgaagagttg gaccgaatga ctcgaccatc                          40

<210> SEQ ID NO 84
<211> LENGTH: 38
<212> TYPE: DNA
<213> ORGANISM: Artificial Sequence
<220> FEATURE:
<223> OTHER INFORMATION: BIP Primer S.typhi

<400> SEQUENCE: 84
cctggggcca atggcatta tgcactaagt aaggctgg                             38

<210> SEQ ID NO 85
<211> LENGTH: 18
<212> TYPE: DNA
<213> ORGANISM: Artificial Sequence
<220> FEATURE:
<223> OTHER INFORMATION: LF Primer S.typhi

<400> SEQUENCE: 85
tcggatggct tcgttcct                                                  18

<210> SEQ ID NO 86
<211> LENGTH: 25
<212> TYPE: DNA
<213> ORGANISM: Artificial Sequence
<220> FEATURE:
<223> OTHER INFORMATION: LB Primer S.typhi

<400> SEQUENCE: 86
caagggtttc aagactaagt ggttc                                          25